United States Patent
Dyson et al.

(10) Patent No.: US 10,781,162 B2
(45) Date of Patent: Sep. 22, 2020

(54) CRYSTALLINE DIETHYLAMINE TETRATHIOMOLYBDATE AND ITS PHARMACEUTICAL USES

(71) Applicant: UCL BUSINESS Ltd, London (GB)

(72) Inventors: Alex Peter Dyson, London (GB); Daniel Gooding, Cambridge (GB); Joanne Holland, Cambridge (GB)

(73) Assignee: UCL Business Ltd, London (GB)

( * ) Notice: Subject to any disclaimer, the term of this patent is extended or adjusted under 35 U.S.C. 154(b) by 0 days.

(21) Appl. No.: 16/340,939

(22) PCT Filed: Oct. 20, 2017

(86) PCT No.: PCT/GB2017/053178
§ 371 (c)(1),
(2) Date: Apr. 10, 2019

(87) PCT Pub. No.: WO2018/073605
PCT Pub. Date: Apr. 26, 2018

(65) Prior Publication Data
US 2019/0233366 A1 Aug. 1, 2019

Related U.S. Application Data

(60) Provisional application No. 62/410,888, filed on Oct. 21, 2016.

(51) Int. Cl.
C07C 211/05 (2006.01)
C07C 209/84 (2006.01)
A61P 9/10 (2006.01)
C07C 209/00 (2006.01)
A61K 9/00 (2006.01)

(52) U.S. Cl.
CPC ............. *C07C 211/05* (2013.01); *A61P 9/10* (2018.01); *C07C 209/00* (2013.01); *C07C 209/84* (2013.01); *A61K 9/0019* (2013.01); *C07B 2200/13* (2013.01)

(58) Field of Classification Search
CPC ... C07C 211/05; C07C 209/00; C07C 209/84; A61P 9/10; A61K 9/0019; C07B 2200/13
USPC ....................................................... 514/663
See application file for complete search history.

(56) References Cited

FOREIGN PATENT DOCUMENTS

WO 2011/121354 A1 10/2011

OTHER PUBLICATIONS

International Search Report dated Jan. 3, 2019 corresponding to International Patent Application No. PCT/GB2017/053178, filed Oct. 20, 2017; 2 pages.

Written Opinion of the ISA dated Jan. 3, 2019 corresponding to International Patent Application No. PCT/GB2017/053178, filed Oct. 20, 2017; 5 pages.
Berhault, Gilles et al., "The Role of Structural Carbon in Transition Metal Sulfides Hydroheating Catalystis," *Journal of Catlysis* (published online Feb. 7, 2001); 198:9-19.
Brewer, George J. et al., "Treatment of Metastatic Cancer with Tetrathiomolybdate, an Anticopper, Antiangiogenic Agent: Phase I Study[1]," *Clinical Cancer Research* (Jan. 2000; accepted Nov. 9, 1999); 6:1-10.
Brewer, George J. et al., "Treatment of Wilson Disease with Ammonium Tetrathiomolybdate," *Arch Neurol* (Apr. 2006); 63:521-527.
Chandrasekaran, J. et al., "Synthesis and Characterization of $[Mo_2(S)_2(\mu\text{-}S)(\eta^2\text{-}S_2)_4]^{2-}$ and Rational Synthesis of $[M_2(L)_2(\mu\text{-}S)(\eta^2\text{-}S_2)_4]^{2-}$ (M= Mo,, W; L=O,S) Anions$^-$," *Inorganic Chemistry, American Chemical Society* (Jan. 1, 1988); 27:3663-3665.
Childs, Ed W., et al., "Hypothermia Reduces Microvascular Permeability and Reactive Oxygen Species Expression after Hemorrhagic Shock," *J Trauma* (2005; accepted for publication Dec. 11, 2003); 58(2):271-277.
Dyson, Alex et al., "Ammonium tetrathiomolybdate following ischemia/reperfusion injury: Chemistry, pharmacology, and impact of a new class of sulfide donor in preclinical injury models," *PLOS Medicine* (https:/doi.org/10.1371/journal.pmed.1002310 Jul. 5, 2017); 24 pages.
Haverich, M.D., Axel et al., "Organ protection during hypothermic circulatory arrest," *J Thorac Cardiovasc Surg* (Mar. 2003; accepted for publication Aug. 15, 2002); 460-462.
L'Her, Erwan et al., "Effects of mild induced hypothermia during experimental sepsis*," *Crit Care Med* (2006; DOI: 10.1097/01.CCM.0000240231.76837.DC); 34(10):2621-2623.
Ning, Xue-Han et al., "Hypothermia preserves myocardial function and mitochondrial protein gene expression during hypoxia," *Am J Physiol Heart Circ Physiol* (Mar. 13, 2003); 285:H212-H219.
Udupa, M. R. et al., "Diethylammonium Molybdates and Tungstates," *J. Indian Chem. Soc.* (Jan. 1976; accepted Sep. 13, 1975); LIII:43-45.

(Continued)

*Primary Examiner* — Kristin A Vajda
(74) *Attorney, Agent, or Firm* — Mintz Levin Cohn Ferris Glovsky and Popeo, P.C.

(57) ABSTRACT

The invention relates to a crystalline diethylamine tetrathiomolybdate salt (DEA-TTM). The invention also relates to methods for producing the crystalline DEA-TTM salt of the invention. The invention also relates to pharmaceutical compositions comprising the crystalline DEA-TTM salt of the invention. The invention also relates to the use of the crystalline DEA-TTM salt of the invention in the treatment of the human or animal body, in particular its use in treatment of a condition requiring reduced metabolism of an organ or the whole body of a patient, by administering to a patient in need thereof a therapeutically effective amount of the crystalline DEA-TTM salt.

14 Claims, 10 Drawing Sheets

(56) References Cited

OTHER PUBLICATIONS

Villar, Jesus et al., "Effects of induced hypothermia in patients with septic adult respiratory distress syndrome," *Resuscitation* (accepted Mar. 23, 1993); 26:183-192.

Wu, Xianren et al., "Systemic Hypothermia, but Not Regional Gut Hypothermia, Improves Survival from Prolonged Hemorrhagic Shock in Rats," *J Trauma* (Oct. 2002; accepted for publication May 29, 2002); 53(4):654-662.

Wu, Xianren et al., "Mild hypothermia during hemorrhagic shock in rats improves survival without significant effects on inflammatory responses," *Crit Care Med* (Jan. 2003); 31(1):195-202.

Xu, Shi et al., "Ammonium Tetrathiomolybdate as a Water-Soluble and Slow-Release Hydrogen Sulfide Donor," *Bioorg Med Chem Lett*. (Mar. 15, 2016); 26(6):1585-1588.

Standard conditions

Thiol dependence pH

Whole blood

CRYSTALLINE DIETHYLAMINE TETRATHIOMOLYBDATE AND ITS PHARMACEUTICAL USES

FIELD OF THE INVENTION

The invention relates to a crystalline diethylamine tetrathiomolybdate salt and pharmaceutical formulations of that crystalline salt. The invention further relates to treatment of conditions requiring modulation of up to three interlinked physiologic systems; metabolism, redox status and inflammation, either within a specific organ or whole body. The invention also relates to treatment of conditions requiring reduced metabolism of an organ or whole body.

BACKGROUND OF THE INVENTION

The majority of disease pathologies are characterised by dysregulation of at least one of three interlinked physiological systems, namely metabolism, redox status and inflammation. Modulation of one or more of these pathways can be used for therapeutic gain; this is supported by a wealth of anecdotal, preclinical and clinical evidence. Having been first described in the 1950s, therapeutic hypothermia, or targeted temperature management, is a recognised example of this, being employed mainly in severe, acute medical emergencies such as cardiac arrest, stroke and trauma. It confers protection by reducing organ metabolism. This in turn increases the tolerance to ischaemia, decreases reactive oxygen species production (during ischaemia and reperfusion) and limits the activation of inflammatory cascades.

Experimental evidence suggests that hypothermia may be beneficial in shock by reducing organ metabolism and increasing the tolerance to ischaemia. Wu et al., J Trauma 2002; 53:654-62, compared regional (gut) and systemic hypothermia on survival in a rat haemorrhage model. They found that inducing systemic hypothermia increased 72 h survival time (100%) compared with regional hypothermia (25%) and normothermia (0%). In a follow-up study, the same group, in Wu et al., Crit Care Med 2003; 31:195-202, showed that hepatic injury was reduced.

Childs et al., J Trauma 2005; 58:271-7, show that hypothermia protects against microvascular barrier dysfunction and reactive oxygen species production. Ning et al., Am J Physiol Heart Circ Physiol 2003; 285:H212-H219, showed improved myocardial performance in isolated rabbit hearts subjected to hypoxia and reoxygenation during hypothermia compared with normothermic controls. Those under hypothermic conditions recovered better in terms of decreased coronary flow, oxygen consumption and developed pressure.

In a rodent model of experimental sepsis induced by caecal ligation and puncture, survival time was inversely proportional to body temperature from 32-42.degree. C.; see L'Her et al., Crit Care Med 2006; 34:2621-3. The utility of hypothermia has also been demonstrated clinically. Hypothermic circulatory arrest is used in some forms of vascular surgery such as aortic arch repair to decrease metabolism and protect against cerebral ischaemia; see Haverich and Hagl., J Thorac Cardiovasc Surg 2003; 125:460-2. In human sepsis associated with the acute respiratory distress syndrome, a subset of moribund patients was subjected to hypothermia as a 'last resort'; hypothermia (32-35.degree. C.) improved survival compared with normothermic septic patients (67% vs 100%); see Villar and Slutsky, Resuscitation 1993; 26:183-92.

Tetrathiomolybdate (TTM) is known to be useful in therapies where reduced core temperature or simulating hypothermia conditions is desirable. EP 2556834 B1, incorporated herein by reference, discloses the use of TTM to treat conditions requiring reduced metabolism of an organ or whole body, e.g. myocardial infarction (MI), stroke or ischaemia-reperfusion injury. The therapy is thus, for example, potentially beneficial in cases of shock such as severe hypoxemia and hemorrhage, trauma (e.g. head injury), in reperfusion injury conditions (such as hemorrhage-reperfusion injury and in elective vascular and cardiac surgery involving interruption and re-institution of blood flow). This treatment may be applicable both in hospital, or en route, e.g. in an ambulance. Clinical applications of particular interest are those surrounding ischaemia-reperfusion injury conditions such as those involving the brain (e.g. stroke, head injury), heart (e.g. during coronary artery bypass surgery and other types of open heart surgery, revascularisation after coronary artery thrombosis), and leg and kidney (e.g. following aortic cross-clamping for peripheral vascular surgery). TTM may be used as such or in the form of a pharmaceutically acceptable salt, for example acid addition salts derived from inorganic or organic acids, such as hydrochlorides, hydrobromides, p-toluenesulphonates, phosphates, sulphates, perchlorates, acetates, trifluoroacetates, propionates, citrates, malonates, succinates, lactates, oxalates, tartrates and benzoates. Salts may also be formed with bases. Such salts include salts derived from inorganic or organic bases, for example alkali metal salts such as magnesium or calcium salts, and organic amine salts such as morpholine, piperidine, dimethylamine or diethylamine salts. One particular salt disclosed in EP 2556834 B1 is ammonium tetrathiomolybdate (ATTM). It has been additionally observed that biological markers of mitochondrial inhibition, synonymous with reduced metabolism, occur in normothermic states with administration of tetrathiomolybdates to rats. Therefore, drug activity is not reliant on a reduced core temperature or simulation of hypothermia.

Ammonium tetrathiomolybdate (ATTM) is known as a therapeutic agent. Brewer et al, Arch Neurol 2006; 63:521-7, discloses that ATTM can be used to treat Wilson's disease, and that it preserves neurological function in patients who present with neurologic disease. Brewer et al, Clin. Cancer Res 2000; 6:1-10, reports that TTM (presumed to be the ammonium salt) may be suitable in therapy of metastatic disease. Its utility apparently derives from its anti-copper activity.

The primary mechanism of modulation of metabolism by ATTM is by slow release of hydrogen sulfide, and subsequent inhibition of the mitochondrial electron transport chain (the main source of reactive oxygen species). Additional mechanisms may include direct scavenging of reactive oxygen species by, and the anti-inflammatory activity of, sulfide. See, Xu, et al., Bioorg. Med. Chem. Lett., 26 (2016) 1585-1588.

To treat conditions requiring reduced metabolism of an organ or whole body, e.g. myocardial infarction (MI), stroke or ischaemia-reperfusion injury, ATTM is typically administered to a patient as an intravenous (IV) solution. The timing and delivery of this invention is critical to prevent further ischaemic damage, thereby requiring a product that can be rapidly reconstituted and administered in an acute critical care setting. More generally a need exists for formulations possessing one or more of the following characteristics relative to other tetrathiomolybdate compositions including improved solubility and shorter dissolution time. In addition, the storage of solid state material and timing of administration following dissolution are crucial, as described herein.

In the treatment of acute conditions, it is vital that a solution of tetrathiomolybdate can be made rapidly in situ (e.g. in a medical facility or in transit to a medical facility, such as in the back of an ambulance) from the active solid material, such that the solution is available for administration (e.g. via the intravenous route) to a patient in the minimum possible time. Thus, it is crucial that the solid form of tetrathiomolybdate utilised for this purpose has a rapid dissolution time in water and/or other physiologically acceptable aqueous media such as saline, 5% glucose solution or Ringer's lactate/Hartmann's solution. The particular salt form of tetrathiomolybdate administered to patients should also have low toxicity. In particular, tetrathiomolybdate is known to act as a sulfide donor in vivo through the release of hydrogen sulfide. It is desirable that this release of hydrogen sulfide predominantly occurs outside of the circulatory system, e.g. intracellularly, and that the amount of hydrogen sulfide released into blood is reduced, since sulfide release or generation within the bloodstream is known to cause toxicity, particularly related to hypotension.

Preparation of a diethyl amine salt of tetrathiomolybdate has been described in a note by Chandrasekaran, et al., *Inorg. Chem.*, 1988, 27, 3663-3665. In this preparation, $H_2MoO_4$ was dissolved in a mixture of water and diethylamine, $Et_2NH$. Hydrogen sulfide, $H_2S$, gas was passed into the solution until the red crystals of $(Et_2NH)_2MoS_4$ separated out, after about 30 minutes. The crystals were washed with cold ethanol and ether and dried under vacuum.

Another preparation of a diethylamine salt of tetrathiomolybdate has been described by Udupa, et al., *J Ind. Chem. Soc.*, 1976, 53, 43-45. In that preparation the interaction of molybdic acid with diethylamine resulted in the isolation of diethylammonium trimolybdate. Passing hydrogen sulfide to a solution of $MoO_3$ in 50% diethylamine, caused the corresponding tetrathiomolybdate, $(DEA)_2MoS_4$, to crystallize out. In Table 1 Udupa et al. report X-ray powder diffraction data for its crystalline $(DEA)_2MoS_4$ having strong peak values of d=8.04 and 7.44. Udupu et al. also reports thermal data for the diethylammonium tetrathiosalts prepared showing a steady decomposition commencing at 120° C. with rapid weight loss up to 250° C. and at around 300° C. the weight loss curve indicate formation of the corresponding metal trisulfide with decomposition at 500° C. to the metal trioxide. Neither Udupa et al. nor Chandrasekaran et al. is however concerned with the preparation of TTM material for clinical use.

Known solid forms of TTM reported in the prior art can suffer from a poor dissolution rate in water or other physiologically acceptable aqueous solutions. There is therefore a pressing clinical need to develop a form of TTM which has both a rapid dissolution rate in water and other physiologically acceptable aqueous solutions, but which also releases low levels of sulfide into the bloodstream of a patient in vivo, for use in the treatment of patients having conditions treatable by tetrathiomolybdate.

SUMMARY OF THE INVENTION

It has surprisingly been found that a new polymorphic form of DEA-TTM has a clinically beneficial balance of properties, namely a rapid dissolution rate in water and other physiologically acceptable aqueous solutions, and the release of low levels of free sulfide into the bloodstream. This new polymorphic form of DEA-TTM is therefore surprisingly useful in the treatment of patients suffering from conditions (especially acute conditions) that require reduced metabolism of an organ or a whole body, e.g. myocardial infarction (MI), stroke or other types of ischaemia-reperfusion injury.

The present invention thus provides a crystalline diethylamine tetrathiomolybdate salt (DEA-TTM). The crystalline DEA-TTM of the invention is characterized by: (i) an XRPD pattern having at least three peaks selected from the peaks at 7.9, 11.4, 12.5, 13.9, 14.9, 20.8 and 21.5±0.5° 2θ; (ii) an XRPD pattern substantially similar to FIG. 1; (iii) a $P2_1$ space group at a temperature of about 100 K; (iv) unit cell dimensions of a=7.1433(4) Å, b=10.7328(5) Å, c=10.7485(8)Å, α=90.00°, β=93.902(6)°, and γ=90.00° at a temperature of about 100 K; or a combination of (i)-(iv).

The present invention also provides a pharmaceutical composition comprising a crystalline diethylamine tetrathiomolybdate salt of the invention and a pharmaceutically acceptable diluent or carrier.

The present invention further provides a crystalline diethylamine tetrathiomolybdate salt of the invention, or a pharmaceutical composition of the invention, for use in the treatment of the human or animal body.

The present invention further provides a crystalline diethylamine tetrathiomolybdate salt of the invention, or a pharmaceutical composition of the invention, for use in the treatment of a condition requiring reduced metabolism of an organ or the whole body of a patient, wherein a therapeutically effective amount of the crystalline salt or pharmaceutical composition is administered to a patient in need thereof.

The present invention further provides a method of treating a human or animal patient, wherein said method comprises administration of a therapeutically effective amount of a crystalline diethylamine tetrathiomolybdate salt of the invention, or a pharmaceutical composition of the invention, to a human or animal patient for treating a condition requiring reduced metabolism of an organ or the whole body of the patient. The condition requiring reduced metabolism may preferably be myocardial infarction (MI), stroke or ischaemia-reperfusion injury.

The present invention further provides the use of a crystalline diethylamine tetrathiomolybdate salt of the invention, or a pharmaceutical composition of the invention, for the manufacture of a medicament for the treatment of a condition requiring reduced metabolism of an organ or the whole body of a human or animal patient.

The present invention also provides a process for making a crystalline diethylamine tetrathiomolybdate salt of the invention, which comprises reacting ammonium tetrathiomolybdate with excess diethylamine, optionally wherein the ammonium tetrathiomolybdate is produced from the reaction of $(NH_4)_6Mo_7O_{24}.4H_2O$ with ammonium sulfide.

The present invention also provides a crystalline diethylamine tetrathiomolybdate salt obtainable by the reaction of ammonium tetrathiomolybdate with excess diethylamine.

BRIEF DESCRIPTION OF THE FIGURES

FIG. 12 shows the pH and thiol dependence of $H_2S$ release from DEA-TTM salts A, B and C. A, B and C denote the synthetic route of manufacture of DEA-TTM, with respect to FIG. 6.

DETAILED DESCRIPTION

Crystalline DEA-TTM Salt

The invention relates to a crystalline diethylamine tetrathiomolybdate salt (DEA-TTM). The crystalline DEA-TTM of the invention is characterized by: (i) an XRPD pattern having at least three peaks selected from the peaks at 7.9, 11.4, 12.5, 13.9, 14.9, 20.8 and 21.5±0.5°2θ; (ii) an XRPD pattern substantially similar to FIG. 1; (iii) a $P2_1$ space group at a temperature of about 100 K; (iv) unit cell dimensions of a=7.1433(4) Å, b=10.7328(5) Å, c=10.7485(8)Å, α=90.00°, β=93.902(6)°, and γ=90.00° at a temperature of about 100 K; or a combination of (i)-(iv).

The preparation of the crystalline DEA-TTM of the invention is described in the examples below.

Typically, the crystalline DEA-TTM of the invention is characterized by an XRPD pattern having at least three peaks selected from the peaks at 7.9, 11.4, 12.5, 13.9, 14.9, 20.8 and 21.5±0.2°2θ, more preferably an XRPD pattern having at least three peaks selected from the peaks at 7.9, 11.4, 12.5, 13.9, 14.9, 20.8 and 21.5±0.1°2θ. Preferably three or more such peaks are observed, more preferably four or more, more preferably five or more, more preferably six or more. Most preferably all such peaks are observed. For example, the crystalline DEA-TTM of the invention may be characterized by an XRPD pattern having peaks at 7.9, 11.4 and 12.5±0.2°2θ, more preferably 7.9, 11.4 and 12.5±0.1° 2θ.

Typically, the peak at 11.4±0.2°2θ, or 11.4±0.1°2θ, is the most intense peak. Preferably, the peak at 11.4±0.2°2θ, or 11.4±0.1°2θ, is at least one and a half times as intense as the next most intense peak. Alternatively, the peak at 11.4±0.2°2θ, or 11.4±0.1°2θ, may be at least twice as intense, three times as intense, four times as intense, or at least five times as intense as the next most intense peak.

Typically, the peak at 11.4±0.2°2θ, or 11.4±0.1°2θ, is at least one and a half times as intense as the peak at 14.9±0.2°2θ, or 14.9±0.1°2θ. Alternatively, the peak at 11.4±0.2°2θ, or 11.4±0.1°2θ, may be at least twice as intense as the peak at 14.9±0.2°2θ, or 14.9±0.1°2θ. Typically, the peak at 11.4±0.2°2θ, or 11.4±0.1°2θ, is at least three times as intense as the peak at 21.5±0.2°2θ, or 21.5±0.1°2θ. Alternatively, the peak at 11.4±0.2°2θ, or 11.4±0.1°2θ, is at least four times as intense, or at least five times as intense, as the peak at 21.5±0.2°2θ, or 21.5±0.1°2θ.

Figure 1:
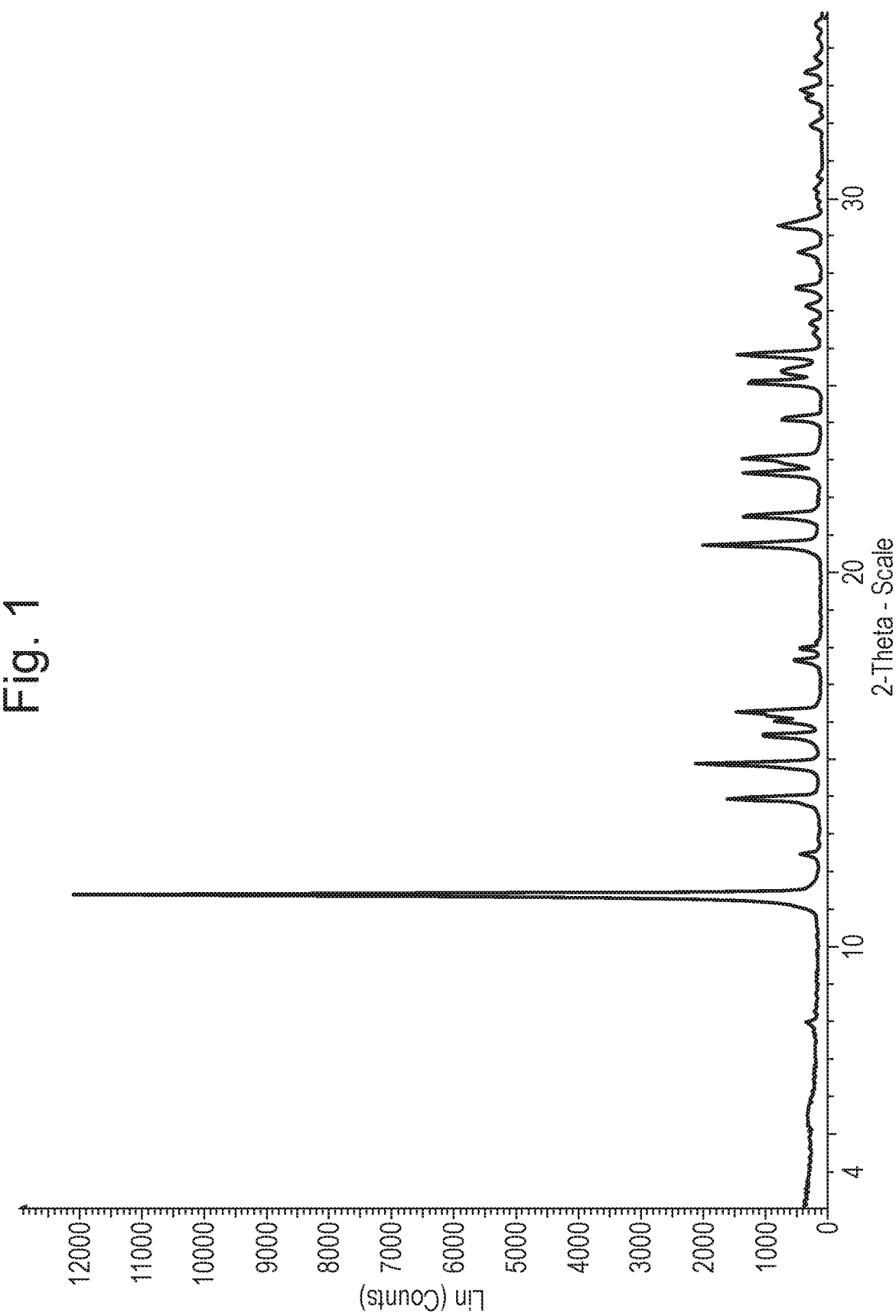
FIG. 1 is the experimental XRPD pattern of the crystalline diethylamine tetrathiomolybdate salt. λ=1.5406 Å.

Typically, the crystalline DEA-TTM of the invention is characterized by an XRPD pattern substantially similar to FIG. 1. Alternatively, the crystalline DEA-TTM of the invention is characterized by an XRPD pattern substantially similar to FIG. 8A.

Typically, the crystalline DEA-TTM of the invention is characterized by a $P2_1$ space group at a temperature of about 100 K. Preferably, the crystalline DEA-TTM of the invention is characterized by a $P2_1$ space group at a temperature of about 100 K and an XRPD pattern having at least three peaks selected from the peaks at 7.9, 11.4, 12.5, 13.9, 14.9, 20.8 and 21.5±0.2° 2θ, more preferably an XRPD pattern having at least three peaks selected from the peaks at 7.9, 11.4, 12.5, 13.9, 14.9, 20.8 and 21.5±0.1°2θ. Alternatively, the crystalline DEA-TTM of the invention is characterized by a $P2_1$ space group at a temperature of about 100 K and an XRPD pattern substantially similar to FIG. 1.

Typically, the crystalline DEA-TTM of the invention is characterized by unit cell dimensions of a=7.1433(4) Å, b=10.7328(5) Å, c=10.7485(8)Å, α=90.00°, β=93.902(6)°, and γ=90.00° at a temperature of about 100 K. Preferably, the crystalline DEA-TTM of the invention is characterized by unit cell dimensions of a=7.1433(4) Å, b=10.7328(5) Å, c=10.7485(8)Å, α=90.00°, β=93.902(6)°, and γ=90.00° at a temperature of about 100 K and an XRPD pattern having at least three peaks selected from the peaks at 7.9, 11.4, 12.5, 13.9, 14.9, 20.8 and 21.5±0.2°2θ, more preferably an XRPD pattern having at least three peaks selected from the peaks at 7.9, 11.4, 12.5, 13.9, 14.9, 20.8 and 21.5±0.1°2θ. Alternatively, the crystalline DEA-TTM of the invention is characterized by unit cell dimensions of a=7.1433(4) Å, b=10.7328(5) Å, c=10.7485(8)Å, α=90.00°, β=93.902(6)°, and γ=90.00° at a temperature of about 100 K and an XRPD pattern substantially similar to FIG. 1. Alternatively, the crystalline DEA-TTM of the invention is characterized by unit cell dimensions of a=7.1433(4) Å, b=10.7328(5) Å, c=10.7485(8)Å, α=90.00°, β=93.902(6)°, and γ=90.00° at a temperature of about 100 K and a $P2_1$ space group at a temperature of about 100 K.

More preferably, the crystalline DEA-TTM of the invention is characterized by unit cell dimensions of a=7.1433(4)

Å, b=10.7328(5) Å, c=10.7485(8)Å, α=90.00°, β=93.902 (6)°, and γ=90.0°° at a temperature of about 100 K, a $P2_1$ space group at a temperature of about 100 K, and an XRPD pattern having at least three peaks selected from the peaks at 7.9, 11.4, 12.5, 13.9, 14.9, 20.8 and 21.5±0.2°2θ, even more preferably an XRPD pattern having at least three peaks selected from the peaks at 7.9, 11.4, 12.5, 13.9, 14.9, 20.8 and 21.5±0.1°2θ. Alternatively, the crystalline DEA-TTM of the invention is characterized by unit cell dimensions of a=7.1433(4) Å, b=10.7328(5) Å, c=10.7485(8)Å, α=90.00°, β=93.902(6)°, and γ=90.00° at a temperature of about 100 K, a $P2_1$ space group at a temperature of about 100 K, and an XRPD pattern substantially similar to FIG. 1.

The crystalline form of the invention is thermally stable. Typically, the crystalline form of the invention is stable at room temperature when packed under argon for at least one month, e.g. one month, two months, three months, six months, one year, two years or more. Typically, the crystalline form of the invention is stable at an elevated temperature of at least 37° C. for at least one week, e.g. one week, two weeks, three weeks, one month, two months, six months or more. The crystalline form of the invention is stable to an oxygen environment. Typically, the crystalline form of the invention is stable in the presence of up to 100% oxygen (e.g. in air) for at least one week, e.g. one week, two weeks, three weeks, one month, two months, six months or more. Typically, the crystalline form of the invention is not hygroscopic.

Manufacture of the Crystalline DEA-TTM Salt of the Invention

The crystalline DEA-TTM of the invention may be prepared by reacting ammonium tetrathiomolybdate (ATTM) with excess diethylamine. Preferably this reaction is carried out in acetonitrile as solvent. Alternatively, the reaction may be carried out in methanol, ethanol, or a mixture of water and acetonitrile as solvent. Preferably this reaction is carried out under an inert atmosphere, e.g. an argon or nitrogen atmosphere. Preferably this reaction is carried out at a temperature of from −78° C. to 150° C., more preferably from 0° C. to 80° C., more preferably from 5° C. to 50° C., more preferably from 10° C. to 40° C., more preferably from 15° C. to 30° C., and most preferably from 20° C. to 25° C., i.e. about room temperature. ATTM itself may be prepared from $(NH_4)_6Mo_7O_{24} \cdot 4H_2O$ in the presence of ammonium sulfide $((NH_4)_2S)$ gas, e.g. as set out in Berhault et al., *Journal of Catalysis*, 2001, 198:9. Thus, the crystalline DEA-TTM of the invention may be prepared in a two-step process: in the first step, $(NH_4)_6Mo_7O_{24} \cdot 4H_2O$ is reacted with ammonium sulfide to produce ATTM; and in the second step, ATTM is reacted with excess dimethylamine to form the crystalline DEA-TTM salt of the present invention.

A detailed exemplar procedure for synthesising the crystalline DEA-TTM salt of the invention is provided in Example 1 below. However, the scope of the present invention is not limited by the Examples.

It has been surprisingly found that the procedure utilised for making the crystalline DEA-TTM of the present invention has advantages over the reported literature procedures used to make other polymorphic forms of crystalline DEA-TTM. In particular, it is noted that the two-step procedure utilised for making the crystalline DEA-TTM of the present invention from $(NH_4)_6Mo_7O_{24} \cdot 4H_2O$ is euthermic. Typically, the rise in temperature over the course of the two-step process when carried out on a scale of less than 50 g (e.g. less than 40 g, less than 30 g, less than 20 g, less than 10 g, or less than 5 g) is less than 20° C., preferably less than 10° C., more preferably less than 7° C., even more preferably less than 5° C., and most preferably about 3° C. or less. In contrast, the preparations of DEA-TTM described in *Inorg. Chem.* 1988, 27, 3663-3665 (discussed above at paragraph [011]) and *J Ind. Chem. Soc.*, 1976, 53, 43-45 (discussed above at paragraph [012]) are both highly exothermic processes, giving temperature rises of over 40° C., even on small scales such as 3 g or 30 g scales. These known literature preparations of DEA-TTM are therefore unsuitable for production of DEA-TTM on a large scale (e.g. kg or tonne scales) due to excessive heat production. These known literature preparations further involve the use of hydrogen sulfide gas, which would also pose additional safety risks when used on a large scale. The process of the present invention does not pose such risks when carried out on a large scale. The process of the present invention is therefore surprisingly more suitable for large-scale production of DEA-TTM than those processes that have been previously reported for preparation of DEA-TTM.

Pharmaceutical Compositions

The present invention also provides a pharmaceutical composition containing crystalline DEA-TTM of the invention in association with a pharmaceutically acceptable diluent or carrier. The purpose of the pharmaceutical composition is to facilitate administration of the compound to an organism in need thereof. As used herein, a pharmaceutically (or physiologically) acceptable diluent or carrier refers to a diluent or carrier that does not cause significant irritation to an organism and does not abrogate the biological activity and properties of the administered compound. Suitable pharmaceutically acceptable diluents and carriers are well known to those skilled in the art.

A pharmaceutical composition of the present invention can take the form of a tablet, a pill, a capsule, a semisolid, a powder, a sustained release formulation, a solution, a suspension, an elixir, an aerosol, a transdermal patch, a bioadhesive film, or any other appropriate composition. The choice of formulation depends on various factors such as the mode of administration.

A particularly preferred embodiment of the invention relates to a pharmaceutical composition containing crystalline DEA-TTM of the invention and water. The pharmaceutical composition may be an aqueous solution of the crystalline DEA-TTM in water or another physiologically acceptable aqueous media such as saline, 5% (w/v) aqueous glucose solution, or Ringer's lactate/Hartmann's solution.

Use of the Crystalline DEA-TTM Salt in the Treatment of Disease

The crystalline DEA-TTM salt of the invention, and/or a pharmaceutical composition comprising the crystalline DEA-TTM salt of the invention, may be used in the treatment of the human or animal body. In general, a pharmaceutical composition of the present invention will be administered to a patient in need thereof so as to deliver to the patient a therapeutically effective amount of the DEA-TTM salt contained therein.

As used herein, the term "therapeutically effective amount" refers to an amount of the DEA-TTM salt which is sufficient to reduce or ameliorate the severity, duration, progression, or onset of a disorder being treated, prevent the advancement of a disorder being treated, cause the regression of, prevent the recurrence, development, onset or progression of a symptom associated with a disorder being treated, or enhance or improve the prophylactic or therapeutic effect(s) of another therapy. The precise amount of DEA-TTM salt administered to a patient will depend on the type and severity of the disease or condition and on the characteristics of the patient, such as general health, age, sex, body weight and tolerance to drugs. It will also depend on the degree, severity and type of the disorder being treated. The skilled artisan will be able to determine appropriate dosages depending on these and other factors.

As used herein, the terms "treat", "treatment" and "treating" refer to the reduction or amelioration of the progression, severity and/or duration of a disorder being treated, or the amelioration of one or more symptoms (preferably, one or more discernible symptoms) of a disorder being treated resulting from the administration of a DEA-TTM salt and/or a pharmaceutical composition according to the invention to a patient.

Typically, the crystalline DEA-TTM salt of the invention, and/or a pharmaceutical composition comprising the crystalline DEA-TTM salt of the invention is/are provided for use in the treatment of a human patient. Preferably, the crystalline DEA-TTM salt of the invention, and/or a pharmaceutical composition comprising the crystalline DEA-TTM salt of the invention is/are provided for use in the treatment of a condition requiring transient reduced metabolism of an organ or the whole body of a patient. Conditions such as myocardial infarction, ischaemic stroke and severe haemorrhage, where perfusion to the affected organ(s) can be significantly compromised, must be salvaged as quickly as possible to minimise the extent of permanent injury. However, the prompt restoration of blood flow to the ischaemic tissue can, in itself, trigger further damage, namely 'reperfusion injury'. This is related to 'oxidative stress', i.e. excess production of reactive species, that arises predominantly from the mitochondria. A transient reduction in mitochondrial activity around the time of reperfusion/revascularization of the blocked feeding blood vessel will significantly reduce the amount of reactive species produced, and thus the degree of tissue damage. It is estimated that up to half of the residual damage after myocardial infarction and coronary revascularization relates to the reperfusion injury phase.

Without wishing to be bound by any particular theory, it is believed that the DEA-TTM salt according to the present invention releases sulfide in vivo in a patient that reduces the production of reactive oxygen species by the mitochondrial electron transport chain. Typically, the condition requiring transient reduced metabolism of an organ or the whole body of a patient is selected from the group consisting of myocardial infarction (MI), ischaemic stroke, severe haemorrhage and reperfusion injury. The condition to be treated may be an acute condition or a chronic condition. Preferably, the condition to be treated is an acute condition. Alternatively, the condition to be treated may be a chronic condition.

Alternatively, the crystalline DEA-TTM salt of the invention, and/or a pharmaceutical composition comprising the crystalline DEA-TTM salt of the invention, may be administered to a patient before, during, or after organ transplantation.

Typically, a therapeutically effective amount of the crystalline DEA-TTM salt and/or a pharmaceutical composition comprising the crystalline DEA-TTM salt of the invention for use in the treatment of the human body is administered to a patient in need thereof dissolved in water or another physiologically acceptable aqueous media such as saline, 5% (w/v) aqueous glucose solution, or Ringer's lactate/Hartmann's solution.

The crystalline DEA-TTM salt and/or a pharmaceutical composition of the invention may be administered by bolus, continuous infusion, or a combination of the two. Thus, in some embodiments, the crystalline DEA-TTM salt and/or a pharmaceutical composition of the invention is administered by bolus. Alternatively, the crystalline DEA-TTM salt and/or a pharmaceutical composition of the invention is administered by continuous infusion. Alternatively, the crystalline DEA-TTM salt and/or a pharmaceutical composition of the invention is administered by a combination of bolus and continuous infusion. The crystalline DEA-TTM salt and/or a pharmaceutical composition of the invention may be administered one or more times per day, for example one, two, three, four, five, six, seven, eight, nine, ten, eleven, twelve or more times per day. The crystalline DEA-TTM salt and/or a pharmaceutical composition of the invention may be administered by any suitable route, e.g. oral, systemic (e.g. transdermal, intranasal, transmucosal or by suppository), or parenteral (e.g. intramuscular, intravenous, or subcutaneous), or directly into an organ's circulation (e.g. intracoronary administration, e.g. following MI). Preferably the crystalline DEA-TTM salt and/or a pharmaceutical composition of the invention is administered by a parenteral route, more preferably intravenously. When administered directly into an organ's circulation (e.g. intracoronary administration), the time period of administration is typically not more than 60 minutes, preferably 1 to 45 minutes, and more preferably still 10 to 30 minutes.

Thus, in a particularly preferred embodiment, the crystalline DEA-TTM salt and/or a pharmaceutical composition of the invention may be administered one or more times per day by bolus, continuous infusion, or a combination of the two, preferably via the intravenous route. Most preferably, the crystalline DEA-TTM salt and/or a pharmaceutical composition of the invention may be administered one or more times per day by bolus followed by a continuous infusion. The continuous infusion may typically be given over a time period of from 1 to 600 minutes, preferably from 2 to 120 minutes, more preferably from 2 to 90 minutes, more preferably from 2 to 45 minutes, and most preferably from 5 to 30 minutes.

A single administration of the crystalline DEA-TTM salt and/or a pharmaceutical composition of the invention may contain, for example, 0.1 to 10.0 mg DEA-TTM/kg body weight, preferably from 0.5 to 5.0 mg DEA-TTM/kg body weight, more preferably from 0.8 to 3.0 mg DEA-TTM/kg body weight, even more preferably from 1.0 to 2.0 mg DEA-TTM/kg body weight, yet more preferably from 1.3 to 1.7 mg DEA-TTM/kg body weight, and most preferably about 1.5 mg DEA-TTM/kg body weight. Typically, this dose for administration will be present in from 1 ml to 1000 ml of water or another physiologically acceptable aqueous media, preferably from 10 ml to 500 ml, more preferably from 50 ml to 250 ml, even more preferably from 80 ml to 150 ml, and most preferably in about 100 ml of water or another physiologically acceptable aqueous media.

Preferably, a single administration of the crystalline DEA-TTM salt and/or a pharmaceutical composition of the invention may contain, for example, 0.1 to 10.0 mg, more preferably 0.8 to 3.0 mg, even more preferably 1.0 to 2.0 mg, yet more preferably 1.3 to 1.7 mg, and most preferably about 1.5 mg DEA-TTM/kg body weight in about 100 ml of an intravenous bolus. Alternatively, a single administration of the crystalline DEA-TTM salt and/or a pharmaceutical composition of the invention may contain, for example, 0.1 to 10.0 mg, more preferably 0.8 to 3.0 mg, even more preferably 1.0 to 2.0 mg, yet more preferably 1.3 to 1.7 mg, and most preferably about 1.5 mg DEA-TTM/kg body weight in about 100 ml of an continuous infusion that is administered over a time period of from 1 to 600 minutes, preferably from 2 to 120 minutes, more preferably from 2 to 90 minutes, more preferably from 2 to 45 minutes, and most preferably from 5 to 30 minutes. In a particularly preferred embodiment, the crystalline DEA-TTM salt and/or a pharmaceutical composition of the invention may be administered one or more times per day by bolus followed by a continuous infusion, wherein the bolus contains 0.1 to 10.0 mg, more preferably 0.8 to 3.0 mg, even more preferably 1.0 to 2.0 mg, yet more preferably 1.3 to 1.7 mg, and most preferably about 1.5 mg DEA-TTM/kg body weight, and the continuous infusion contains 0.1 to 10.0 mg, more preferably 0.8 to 3.0 mg, even more preferably 1.0 to 2.0 mg, yet more preferably 1.3 to 1.7 mg, and most preferably about 1.5 mg DEA-TTM/kg body weight and is administered over a time period of from 1 to 600 minutes, preferably from 2 to 120 minutes, more preferably from 2 to 90 minutes, more preferably from 2 to 45 minutes, and most preferably from 5 to 30 minutes.

The present invention also therefore provides a method to treat a condition requiring reduced metabolism of an organ or the whole body of a patient. The condition requiring reduced metabolism may be myocardial infarction (MI), stroke or ischaemia-reperfusion injury. A method of the invention administers to a patient in need thereof a therapeutically effective amount of a pharmaceutical composition containing crystalline DEA-TTM of the invention dissolved in water or another physiologically acceptable aqueous media such as saline, 5% (w/v) glucose solution or Ringer's lactate/Hartmann's solution. The pharmaceutical composition may be administered one or more times per day by bolus, continuous infusion, or a combination of the two, preferably via the intravenous route. For example, the pharmaceutical composition to be administered may contain 0.1 to 10 mg DEA-TTM/kg body weight in a 100 ml intravenous (IV) bolus. A method of the invention may also include, prior to administering the pharmaceutical composition the step of combining crystalline DEA-TTM with water or another physiologically acceptable aqueous media such as saline or phosphate buffered saline (PBS).

The present invention also provides the use of a crystalline DEA-TTM salt according to the invention for the manufacture of a medicament for the treatment of a condition in a human or animal patient, preferably wherein the condition to be treated is a condition requiring reduced metabolism of an organ or the whole body of a patient, more preferably wherein the condition requiring reduced metabolism is myocardial infarction (MI), stroke or any other type of ischaemia-reperfusion injury.

The crystalline DEA-TTM salt and/or a pharmaceutical composition of the present invention may also be used in combination with one or more other drugs or pharmaceutical compositions in the treatment of disease or conditions for which the crystalline DEA-TTM salt and/or a pharmaceutical composition of the present invention and/or the other drugs or pharmaceutical compositions may have utility. The one or more other drugs or pharmaceutical compositions may be administered to the patient by any one or more of the following routes: oral, systemic (e.g. transdermal, intranasal, transmucosal or by suppository), or parenteral (e.g. intramuscular, intravenous or subcutaneous). Compositions of the one or more other drugs or pharmaceutical compositions can take the form of tablets, pills, capsules, semisolids, powders, sustained release formulations, solutions, suspensions, elixirs, aerosols, transdermal patches, bioadhesive films, or any other appropriate compositions. The choice of formulation depends on various factors such as the mode of drug administration (e.g. for oral administration, formulations in the form of tablets, pills or capsules are preferred) and the bioavailability of the drug substance.

The crystalline DEA-TTM salt and/or a pharmaceutical composition of the present invention is particularly advantageous for use in the treatment of disease in a patient, in particular for use in the treatment of acute conditions requiring reduced metabolism of an organ or the whole body of a patient, when compared with other forms of TTM. In particular, the DEA-TTM polymorph of the present invention was unexpectedly found to have a high solubility in water at 25° C. of approximately 110 mg/ml. In contrast, other known polymorphs of DEA-TTM have a solubility of less than 105 mg/ml in water at 25° C., and ATTM has a solubility of only 2 mg/ml in water at 25° C. The DEA-TTM polymorph of the present invention also releases a low amount of $H_2S$ into the bloodstream of a patient. A combination of these features makes the DEA-TTM polymorph of the present invention surprisingly highly suited to its desired clinical use, since tetrathiomolybdate solutions for use in treating acute conditions (e.g. acute ischaemia) may have to be made rapidly in situ, e.g. in the back of an ambulance during transport of the patient to hospital or other medical facility, and should not be toxic to patients via release of unacceptably high levels of $H_2S$ into the bloodstream.

The publications, patent publications and other patent documents cited herein are entirely incorporated by reference. Herein, any reference to a term in the singular also encompasses its plural. Where the term "comprising", "comprise" or "comprises" is used, said term may substituted by "consisting of", "consist of" or "consists of" respectively, or by "consisting essentially of", "consist essentially of" or "consists essentially of" respectively. Any reference to a numerical range or single numerical value also includes values that are about that range or single value. Unless otherwise indicated, any % value is based on the relative weight of the component or components in question.

The following are Examples that illustrate the present invention. However, these Examples are in no way intended to limit the scope of the invention.

EXAMPLES

The following analytical methods were used to characterize the diethylamine tetrathiomolybdate salt of the invention. For work done at room temperature (RT) that is generally about 25° C.

Single Crystal X-Ray Diffraction (SCXRD): Data were collected on an Oxford Diffraction SuperNova Dual source, Cu at zero, Atlas CCD Diffractometer equipped with an Oxford Cryosystems Cryostream cooling device. Structures were solved using the Bruker SHELXTL program and refined with the SHELXTL program as part of the Bruker SHHXTL suite. Unless otherwise stated, hydrogen atoms attached to carbon were placed geometrically and allowed to refine with a riding isotropic displacement parameter.

Differential Scanning Calorimetry (DSC): DSC data were collected on a PerkinEimer Pyris 4000 DSC equipped with a 45 position sample holder. The instrument was verified for energy and temperature calibration using certified indium. A predefined amount of the sample, 0.5-3.0 mg, was placed in a pin holed aluminium pan and heated at 20° C./min from 30 to 300° C. A purge of dry nitrogen at 60 ml·min$^{-1}$ was maintained over the sample. The instrument control, data acquisition and analysis were performed with Pyris Software v9.0.1.0203.

Example 1: Crystalline Diethylamine Tetrathiomolybdate Salt (DEA-TTM)

1.1 Preparation of Crystalline DEA-TTM

Ammonium tetrathiomolybdate (5 g) was weighed into a glass round bottomed flask under argon. Acetonitrile (25 ml) was added to the flask. The resulting slurry was stirred whilst a large excess of diethylamine was added at room temperature whilst maintaining the argon atmosphere. After 4 hours, argon was bubbled through the resulting solution to drive off the excess diethylamine and the majority of the acetonitrile. Once the solvent volume was reduced to ca. 5 ml, the product was then filtered under vacuum and the resulting red crystals washed with ether, prior to drying in a vacuum oven at 40° C. overnight.

1.2 XRPD Characterisation of Crystalline DEA-TTM

X-ray Powder Diffraction (XRPD) Characterisation: X-Ray Powder Diffraction patterns were collected on a PANalytical diffractometer using Cu Kα radiation (λ=1.5406 Å) (45 kV, 40 mA), θ-θ goniometer, focusing mirror, divergence slit (½"), soller slits at both incident and divergent beam (4 mm) and a PIXcel detector. The software used for data collection was X'Pert Data Collector, version 2.2f and the data was presented using X'Pert Data Viewer, version 1.2d. Instrument verification was performed using a silicon and benzoic acid standard, performed with the same batch program as listed below for sample analysis. Samples were run under ambient conditions and were analysed by transmission foil XRPD, using the powder as received. Approximately 2-5 mg of the sample was mounted on a 96-position sample plate supported on a polyimide (Kapton, 12.7 μm thickness) film. Plate height (Z) was set to 9 mm. Data was collected in the range 3-40° 2θ with a continuous scan (speed of 0.2° 2θ/s).

The experimental XRPD pattern of the diethylamine tetrathiomolybdate salt is shown in FIG. 1. Table 1 lists the angles, °2θ±0.2°2θ, and d-spacing of the peaks identified in the experimental XRPD pattern of FIG. 1. The entire list of peaks, or a subset thereof, may be sufficient to characterize the salt. For example, the crystalline salt may be characterised by at least three of seven peaks selected from the peaks at 7.9, 11.4, 12.5, 13.9, 14.9, 20.8 and 21.5±0.5°2θ as well as by an XRPD pattern substantially similar to FIG. 1.

TABLE 1

| Angle °2θ ± 0.2 °2θ | d value Angstrom | Intensity % |
|---|---|---|
| 7.9 | 11.12 | 2.8 |
| 11.4 | 7.79 | 100.0 |
| 12.5 | 7.10 | 3.4 |
| 13.9 | 6.35 | 13.2 |
| 14.9 | 5.96 | 17.4 |
| 15.6 | 5.66 | 8.5 |
| 16.0 | 5.52 | 6.9 |
| 16.2 | 5.45 | 12.0 |
| 17.6 | 5.02 | 4.3 |
| 18.0 | 4.93 | 3.5 |
| 20.8 | 4.28 | 16.4 |
| 21.5 | 4.13 | 11.1 |
| 22.7 | 3.92 | 11.1 |
| 23.1 | 3.85 | 11.2 |
| 24.1 | 3.69 | 5.9 |
| 25.1 | 3.55 | 10.3 |
| 25.4 | 3.50 | 6.0 |
| 25.8 | 3.44 | 12.0 |
| 26.7 | 3.34 | 2.3 |
| 27.1 | 3.28 | 2.8 |
| 27.6 | 3.22 | 4.0 |
| 28.6 | 3.12 | 3.7 |
| 29.3 | 3.04 | 6.5 |
| 32.0 | 2.80 | 2.1 |
| 32.7 | 2.74 | 2.7 |
| 32.9 | 2.72 | 3.4 |
| 33.4 | 2.68 | 2.8 |

1.3 SCXRD Characterisation of the Crystalline DEA-TTM

The crystal used for single crystal structure determination was prepared from Ammonium tetrathiomolybdate (5 g), which was weighed into a glass round bottomed flask under argon. Acetonitrile (25 ml) was added to the flask. The resulting slurry was stirred whilst a large excess of diethylamine was added at room temperature whilst maintaining the argon atmosphere. After 4 hours, argon was bubbled slowly through the resulting solution to drive off the excess diethylamine and the majority of the acetonitrile. Once the solvent volume was reduced to ca. 20 ml, the resulting red liquid was poured into an evaporation dish, where any remaining solvent or excess diethylamine product was allowed to evaporate slowly. Large cubic red crystals resulted, which were washed with ether, prior to drying in a vacuum oven at 40° C. overnight. A suitable single crystal was isolated from the crystals which formed by this method.

Figure 2:
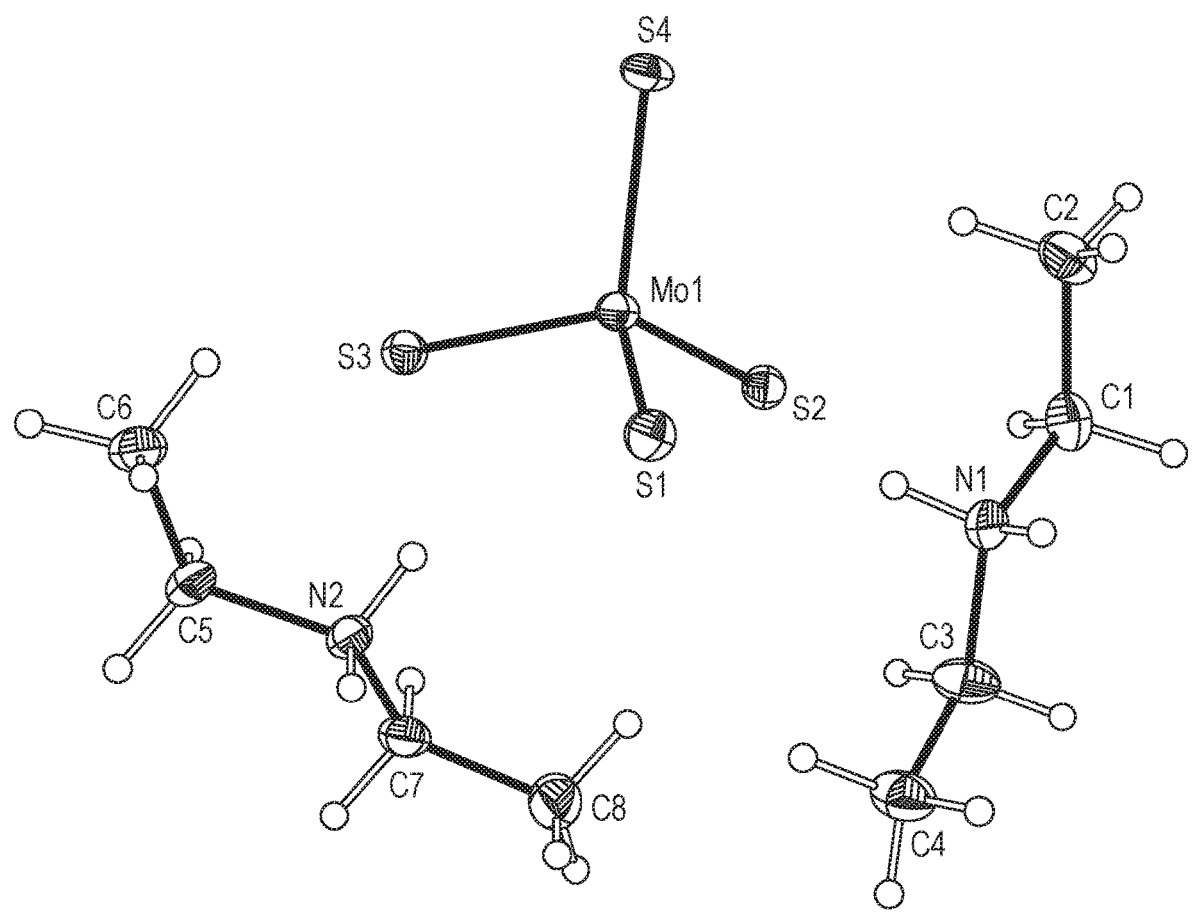
FIG. 2 shows an ORTEP drawing of the crystalline diethylamine tetrathiomolybdate salt at 100 K.
Figure 3:
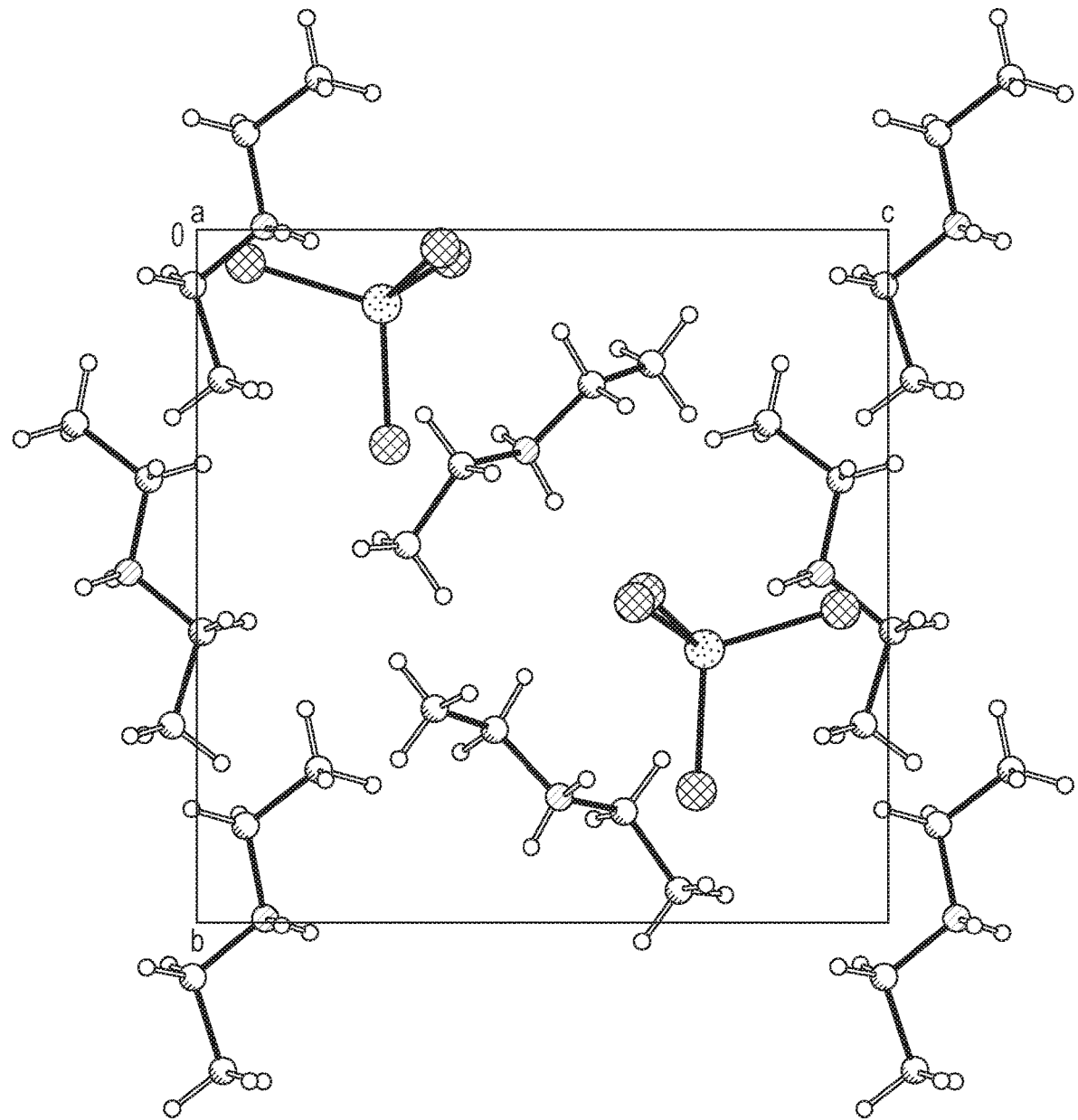
FIG. 3 is a packing diagram for the crystalline diethylamine tetrathiomolybdate salt at 100 K, with hydrogen bonds shown as dashed lines, viewed down the a-axis of the unit cell.

The single crystal data and structure refinement parameters for the structure measured at 100 K are reported in Table 2, below. FIG. 2 shows an ORTEP diagram of the diethylamine tetrathiomolybdate salt at 100 K showing the numbering scheme employed. A packing diagram for the diethylamine tetrathiomolybdate salt at 100 K, with hydrogen bonds shown as dashed lines, viewed down the a-axis of the unit cell is shown in FIG. 3.

Crystal data presented in Table 2 may also be used to characterize diethylamine tetrathiomolybdate salt of the invention. The salt may be characterized by parameters such as its space group or its unit cell dimensions, e.g., by a P2$_1$ space group at a temperature of about 100 K; or unit cell dimensions of a=7.1433(4) Å, b=10.7328(5) Å, c=10.7485(8)Å, α=90.00°, β=93.902(6)°, and γ=90.00° at a temperature of about 100 K.

TABLE 2

| | |
|---|---|
| Molecular formula | C$_8$H$_{24}$Mo$_1$N$_2$S$_4$ |
| Molecular weight | 372.47 |
| Crystal System | Monoclinic |
| Space Group | P2$_1$ |
| Unit Cell Dimensions | a = 7.1433(4) Å |
| | b = 10.7328(5) Å |
| | c = 10.7485(8) Å |
| | α = 90.00° |
| | β = 93.902(6)° |
| | γ = 90.00° |
| Cell Volume | 822.16(8) Å$^3$ |
| Z | 2 |
| Temperature | 100(1) K |
| Radiation Wavelength/type | 0.71073 Å/MoKα |
| Goodness of fit | 1.011 |
| R factor | 0.0311 |
| Morphology | Black prism |

Figure 4:
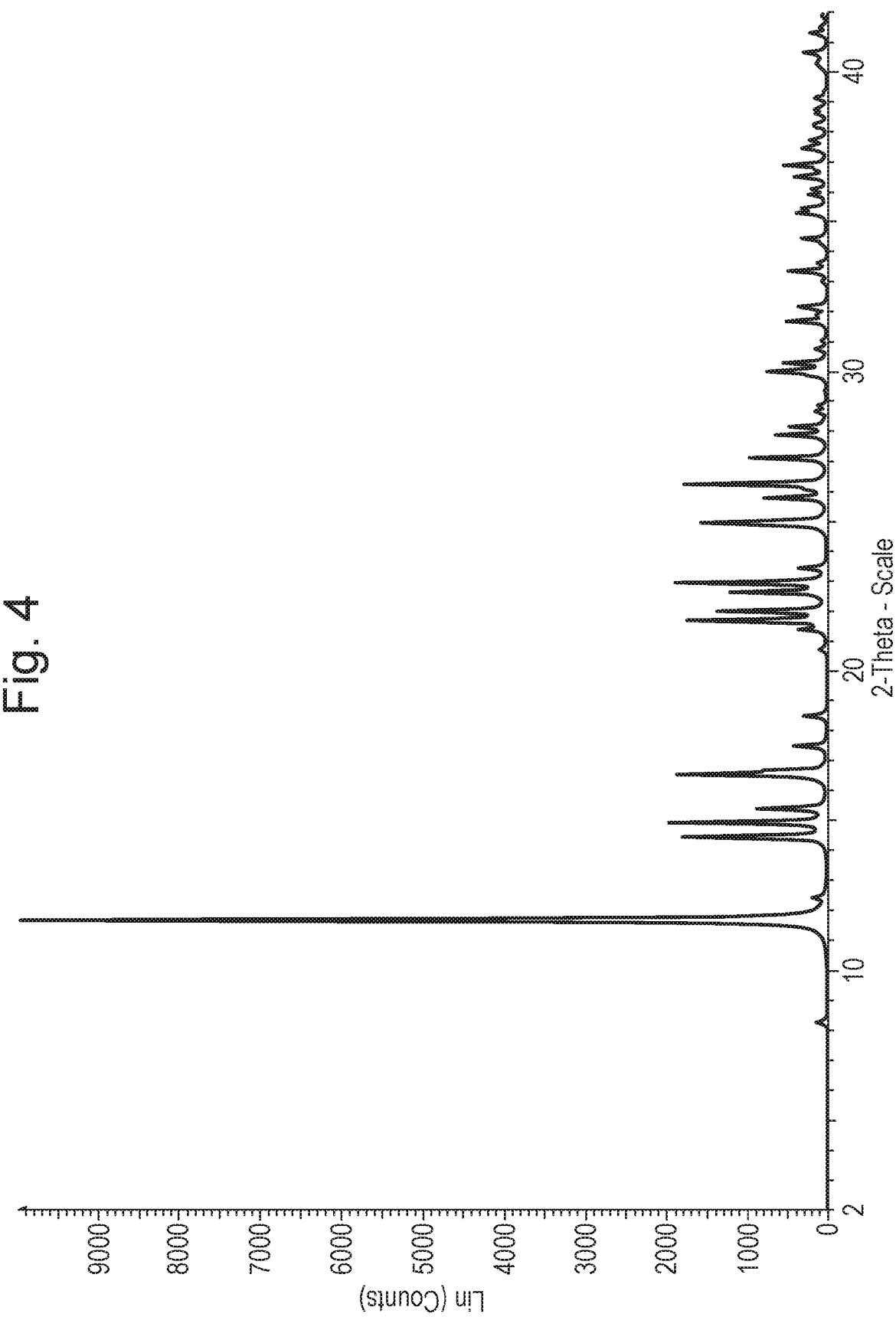
FIG. 4 depicts the calculated XRPD pattern based on the single crystal data and structure for crystalline diethylamine tetrathiomolybdate salt at 100 K.

The calculated XRPD pattern based on the single crystal data and structure for the diethylamine tetrathiomolybdate salt at 100 K is shown in FIG. 4. It is also noted that there are some small temperature shifts in some of the peaks owing to the fact that the experimental XRPD pattern was collected at room temperature and the calculated XRPD pattern is derived from data collected at 100 K. There are also small intensity differences owing to preferred orientation effects, present in the experimental pattern.

1.4 Differential Scanning Calorimetry (DSC) of the Crystalline DEA-TTM

Figure 5:
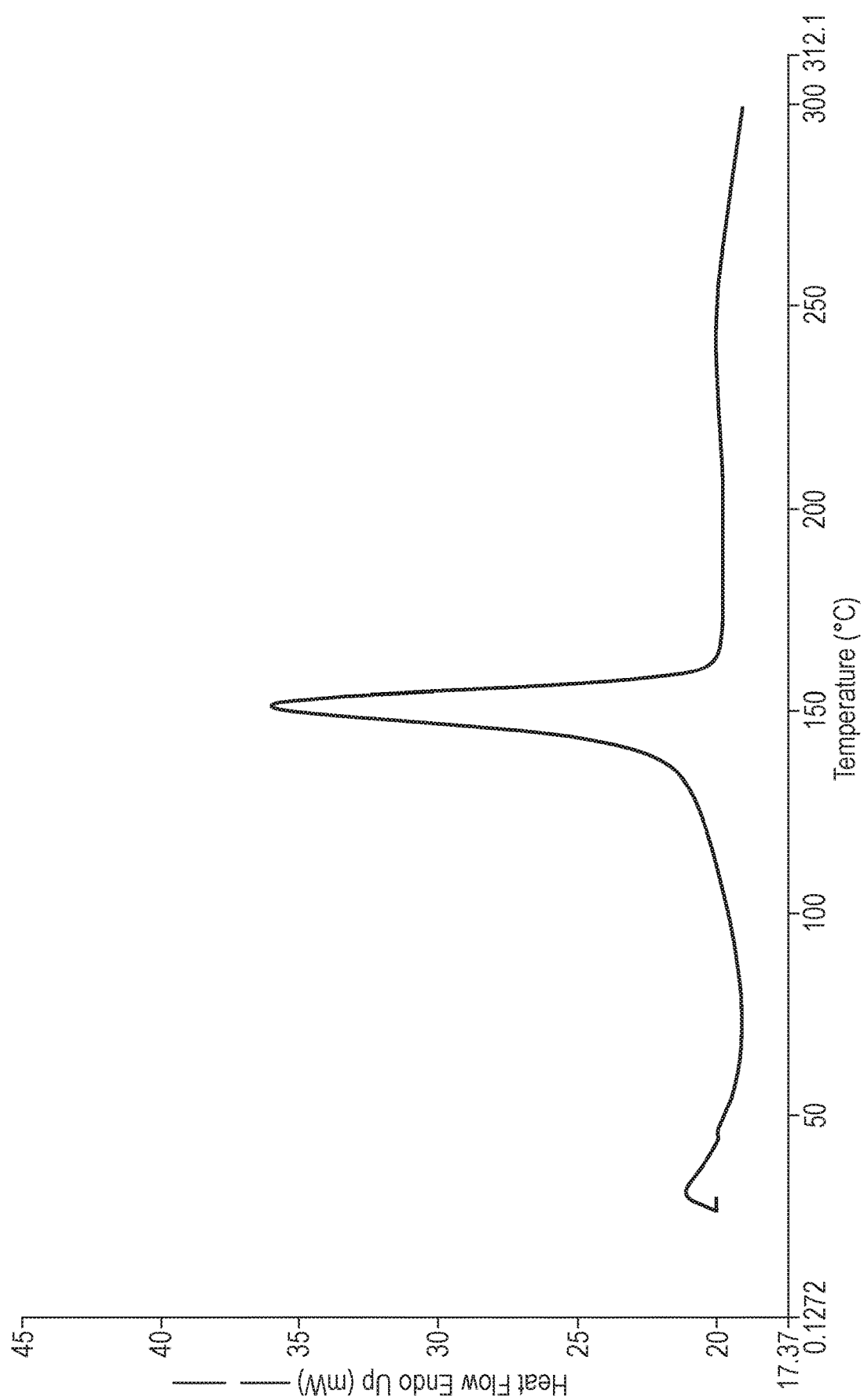
FIG. 5 shows the differential scanning calorimetry (DSC) trace obtained for the crystalline diethylamine tetrathiomolybdate salt.

The differential scanning calorimetry (DSC) trace obtained for the diethylamine tetrathiomolybdate salt is shown in FIG. 5. A single isotherm is observed over with a peak maximum of 151.4° C.

1.5 Preparation of Known Polymorphs of DEA-TTM

Figure 6:
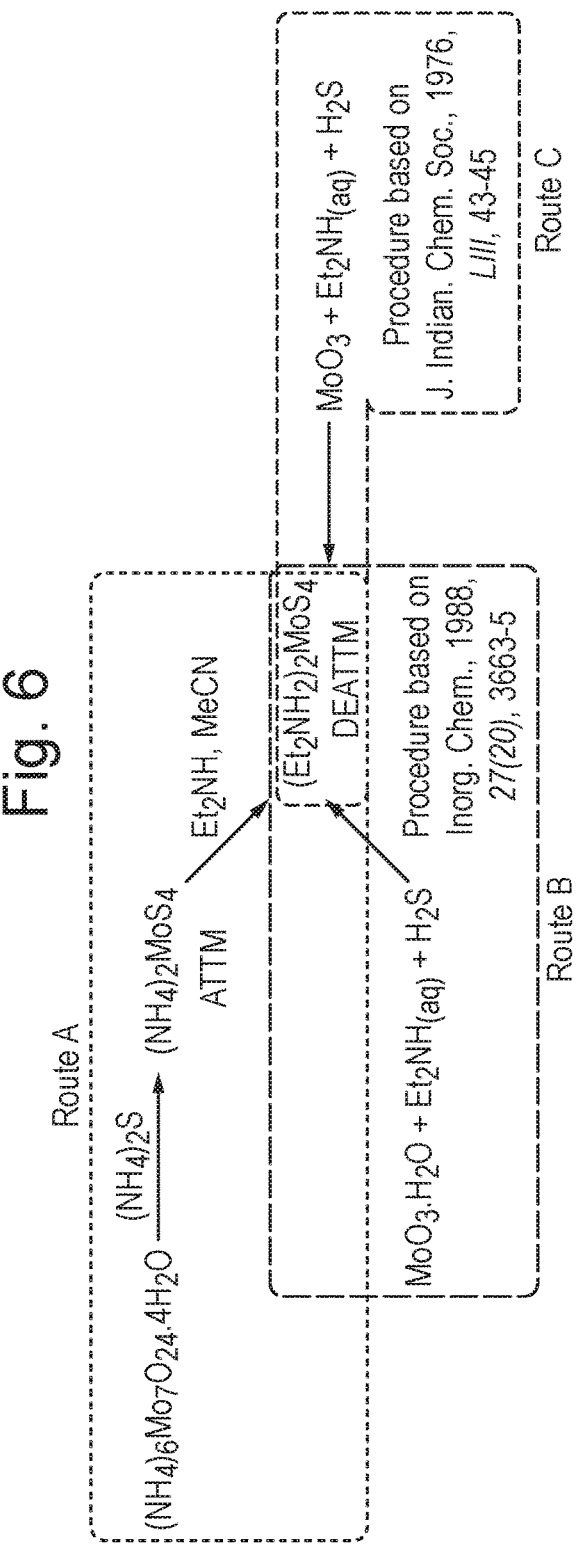
FIG. 6 outlines the different synthetic routes A, B and C to different polymorphic salt forms of DEA-TTM. ATTM=ammonium tetrathiomolybdate; $Et_2NH$=diethylamine; $H_2S$=gaseous hydrogen sulfide; MeCN=acetonitrile; $MoO_3.H_2O$=molybdic acid; $(NH_4)_6Mo_7O_{24}.4H_2O$=ammonium heptamolybdate tetrahydrate; $(NH_4)_2S$=ammonium sulfide; 'aq' denotes aqueous.

Another sample of the DEA-TTM salt of the present invention was synthesised alongside samples of two known DEA-TTM salts (Almac Sciences, Northern Ireland). An overview of the synthetic routes to each of these salts is shown in FIG. 6.

Preparation of the DEA-TTM salt of the present invention (hereinafter referred to as DEA-TTM salt A) was effected in two steps from $(NH_4)_6Mo_7O_{24}.4H_2O$. In the first step, $(NH_4)_6Mo_7O_{24}.4H_2O$ was treated with ammonium sulfide, $(NH_4)_2S$, in order to produce ammonium tetrathiomolybdate (ATTM), $(NH_4)_2MoS_4$. In the first step, ATTM was synthesised according to the procedure set out in Berhault et al., *Journal of Catalysis*, 2001, 198:9. In the second step, ATTM was converted to DEA-TTM using the protocol set out in section 1.1 above.

Preparation of a DEA-TTM salt was also carried out from molybdic acid in accordance with the published procedure set out in Chandrasekaran, et al., *Inorg. Chem.*, 1988, 27, 3663-3665, and discussed above at paragraph [011]. The salt prepared in this process is hereinafter referred to as DEA-TTM salt B.

Preparation of a DEA-TTM salt was also carried out from molybdenum trioxide in accordance with the published procedure set out in Udupa, et al., *J. Ind. Chem. Soc.*, 1976, 53, 43-45, and discussed above at paragraph [012]. The salt prepared in this process is hereinafter referred to as DEA-TTM salt C.

Figure 7:
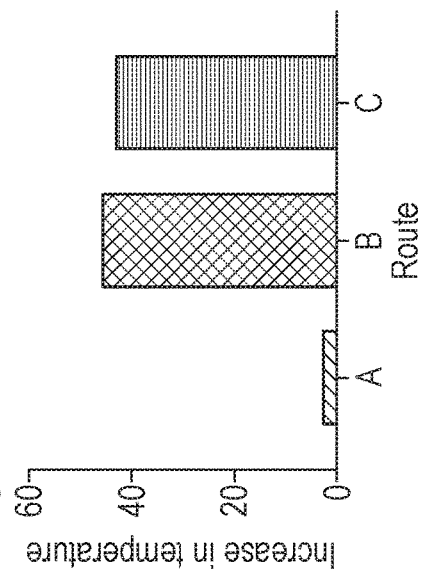
FIG. 7 shows the exothermicity of synthetic routes A, B and C to DEA-TTM.

Synthesis by the different routes revealed striking differences in exothermicity. Route A (at both 4 g and 30 g scales) was minimally exothermic, with an increase in temperature of 3° C. (see FIG. 7). By contrast, administration of $H_2S$ gas through solutions containing molybdic acid or molybdenum trioxide (at both 3 g and 30 g scales, final product) generated significant heat (>40° C.). The exothermicity of routes B and C would limit any further scale-up by these routes due to safety concerns. Furthermore, Routes B and C require the use of hydrogen sulfide ($H_2S$) gas that poses additional safety risks. Attempts to control the exotherm from Routes B and C by cooling the reaction vessel led to either poor yield or no product being isolated.

1.6 Comparative Analysis of the Chemical Structures of DEA-TTM Salts A, B and C

DEA-TTM salts A, B and C were subjected to analysis by high performance liquid chromatography (HPLC) to determine purity, inductively coupled plasma mass spectrometry (ICP-MS) to determine molybdenum content, elemental analysis and X-ray powder diffraction (XRPD).

XRPD analyses were performed using a Panalytical Xpert Pro diffractometer equipped with a Cu X-ray tube (radiation parameters as follows: K-Alpha1: 1.54060 Å; K-Alpha2: 1.54443 Å; K-Beta: 1.39225 Å; K-A2/KA-1 ratio: 0.5) and a Pixcel detector system. The samples were analysed at ambient temperature in transmission mode and held between low density polyethylene films. The Almac default XRPD program was used (range 3-40° 2θ, step size 0.013°, counting time 99 sec, ~5 min run time). XRPD patterns were sorted and manipulated using HighScore Plus 2.2c software.

The results of the HPLC, ICP-MS and elemental analysis for the DEA-TTM salts produced via routes A, B and C are shown in Table 3 below, and yield comparable results for each of the different salt forms of DEA-TTM.

TABLE 3

| Route | % purity (HPLC) | Mo content (%) (ICP-MS) | Elementary analysis (w/w) (%) | | | |
|---|---|---|---|---|---|---|
| | | | C | H | N | S |
| A | 95.94 | 22.0 | 25.86 | 6.50 | 7.47 | 34.58 |
| B | 94.62 | 22.4 | 25.84 | 6.48 | 7.48 | 33.57 |
| C | 93.23 | 26.3 | 25.89 | 6.51 | 7.47 | 34.40 |

Figure 8A:
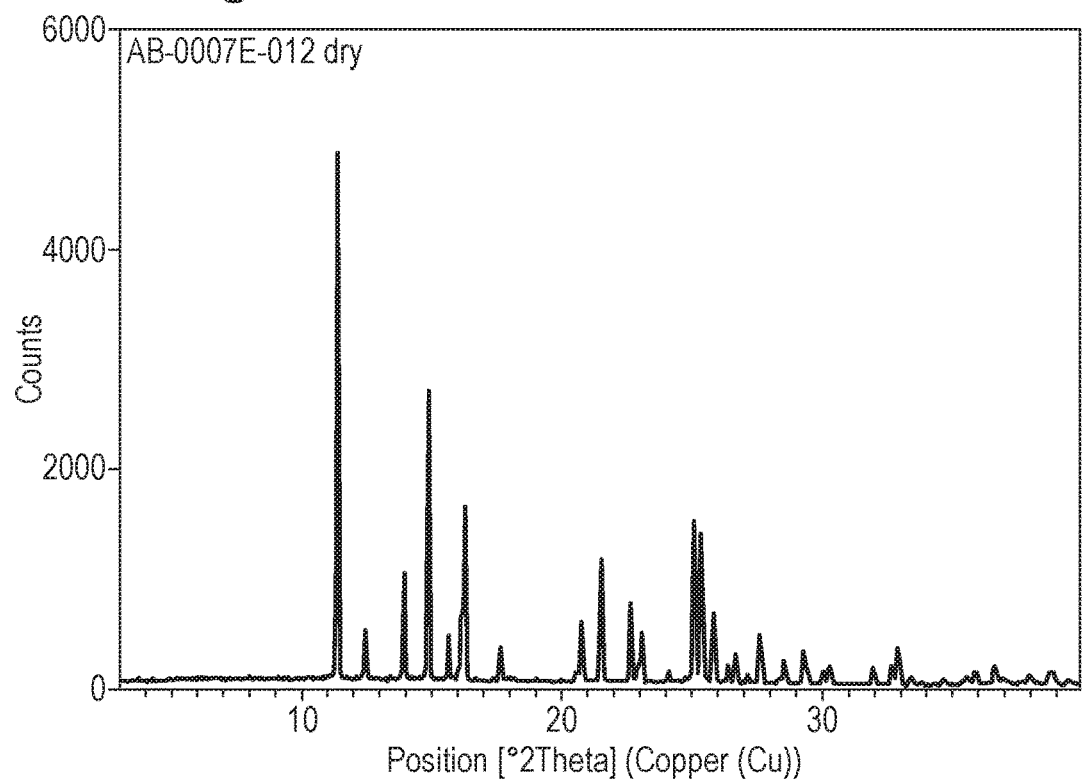
FIGS. 8A, 8B and 8C are the experimental XRPD patterns of the crystalline DEA-TTM salts synthesised from routes A, B and C respectively. λ=1.5406 Å.
Figure 8B:
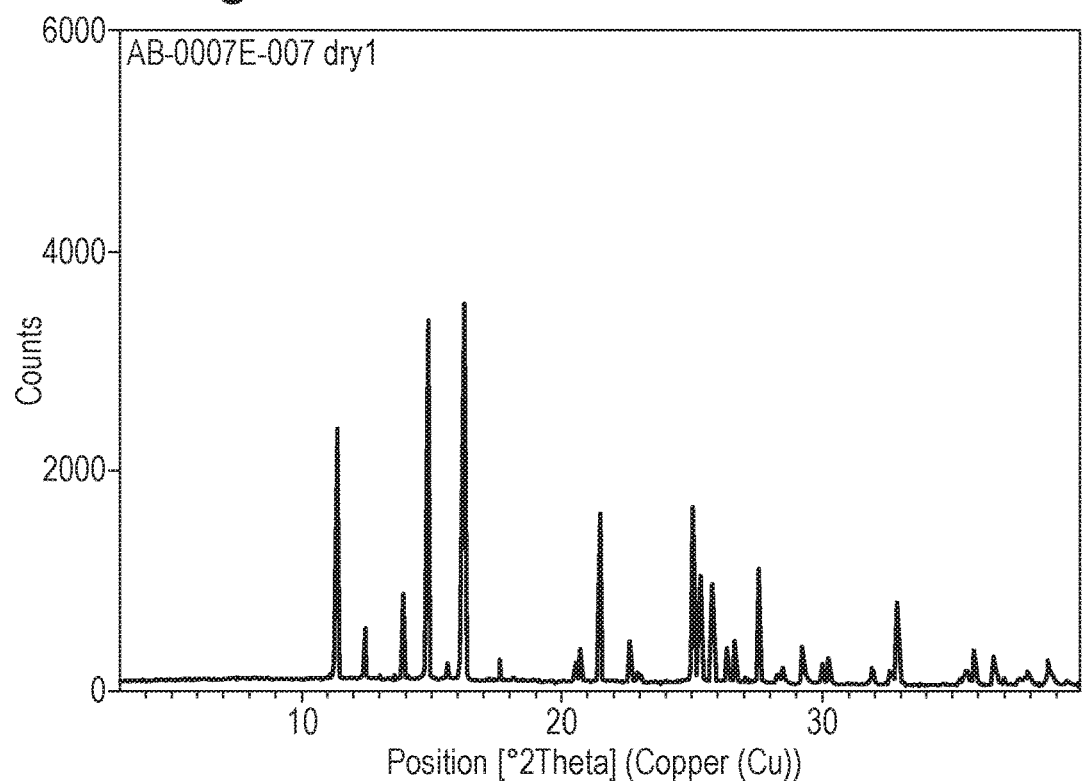
Figure 8C:
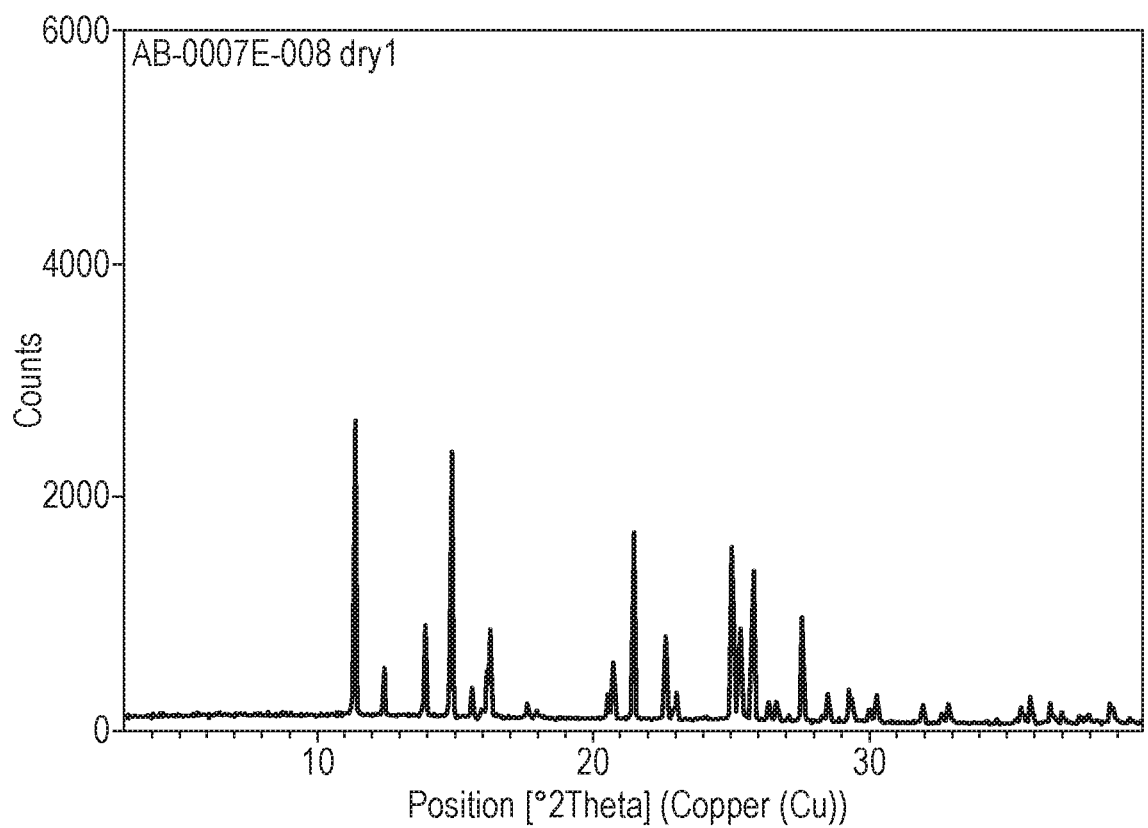

The XRPD patterns for each of the DEA-TTM salts are shown in FIG. 8A-8C. Analysis of samples by XPRD showed the three forms to have similar, but not identical, chemical signatures. Notable differences include an additional peak for route A at 7.9°2θ (see FIG. 8A; this peak can also be clearly observed in FIG. 1). Additionally, the intensity of the peak at 11.4°2θ compared to that at 14.9°2θ differs between the DEA-TTM salts. For DEA-TTM synthesised by route A, the intensity of the 11.4°2θ peak is twice as large as the intensity of the peak at 14.9°2θ. In contrast, for DEA-TTM synthesised by route C (see FIG. 8C), the intensity of the 11.4°2θ peak is only 5% larger than the intensity of the peak at 14.9°2θ, and for DEA-TTM synthesised by route B (see FIG. 8B), the peak at 14.9°2θ was more intense than the peak at 11.4°2θ.

Example 2: Attempted Preparation of Other Crystalline Forms of Tetrathiomolybdate (Comparative)

Attempts to prepare other diethylamine (DEA) crystalline salts of tetrathiomolybdate were done using a slurry method as described below. The DEA salt former, the solvent, the method used and the results are described in Table 4. No other crystalline form was prepared.

Slurry method: A 1:1 molar ratio of ammonium tetrathiomolybdate and the target salt former totaling 200 mg were placed in a 4 ml glass vial. 2 ml of chosen solvent was added to the vial. The vial was agitated for 24 hours, after which the solids were filtered, dried under vacuum and examined by XRPD.

TABLE 4

| Salt Former | Solvent | Method | Result |
|---|---|---|---|
| Diethylamine | Water/Acetonitrile | Slurry | No change by XRPD |
| Diethylamine | Methanol | Slurry | No change by XRPD |
| Diethylamine | Ethanol | Slurry | No change by XRPD |

Example 3: DEA-TTM Dissolution and Solubility Study

The in vitro dissolution and aqueous solubility behaviour of the diethylamine tetrathiomolybdate crystalline salt compared with that of the pure ammonium tetrathiomolybdate salt (purchased from Sigma Aldrich) was examined in distilled water. The dissolution experiment was carried out in triplicate on both the diethyl tetrathiomolybdate salt and the ammonium tetrathiomolybdate salt. The solubility of the pure ammonium tetrathiomolybdate salt in distilled water was found to be ca. 2 mg/ml and dissolution took over 1 hour. The solubility of the pure diethylamine tetrathiomolybdate salt in distilled water was found to be >100 mg/ml whereas dissolution was complete within a minute.

Figure 9:
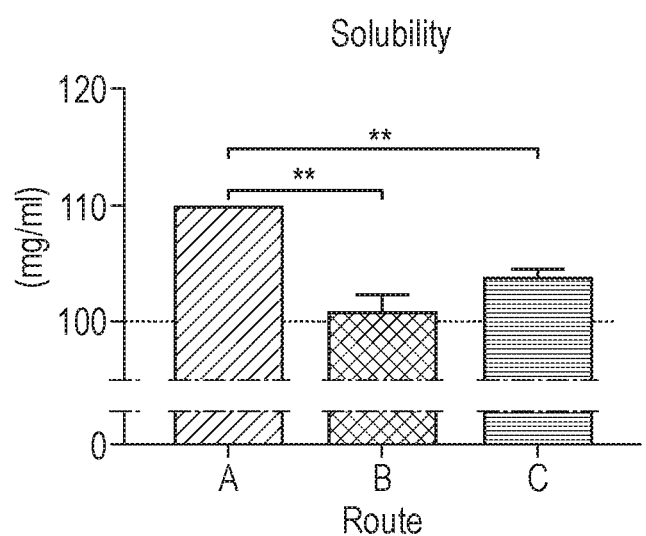
FIG. 9 shows the solubility of each of the DEA-TTM salts A, B and C in water at 25° C. n=2/group. ** denotes P<0.01 using one-way ANOVA followed by Tukey's multiple comparisons test.

The in vitro dissolution and aqueous solubility behaviour at 25° C. was also investigated for the DEA-TTM salts synthesised by routes A, B and C as outlined in Example 1.5 above (Almac Sciences, Northern Ireland). The results are shown in FIG. 9. DEA-TTM salt A shows a superior solubility to DEA-TTM salts B and C, with the differences being statistically significant (P<0.01). This is of particular clinical significance for the reasons discussed in paragraph [015] above.

Figure 10:
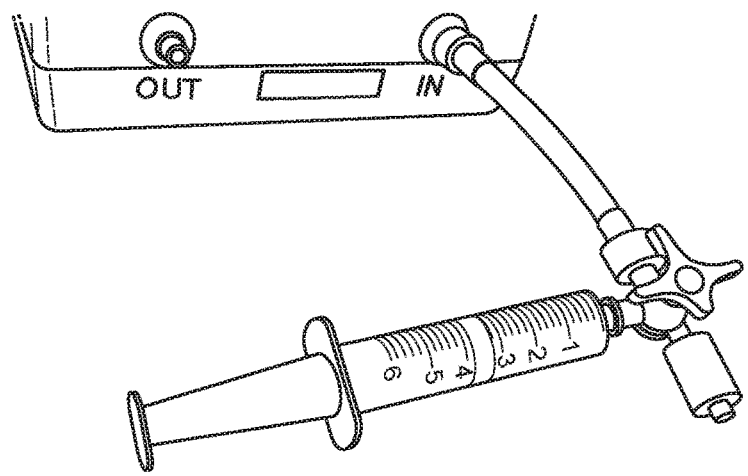
FIG. 10 illustrates the apparatus for the $H_2S$ gas detection assay.

Example 4: $H_2S$ Gas Release from DEA-TTM Salts A, B and C 4.1 Test for $H_2S$ Gas Release Free (biologically active) sulfide constitutes $H_2S$ gas and two anions, $HS^-$ and $S^{2-}$. An assay for quantifying $H_2S$ gas release was developed by Dyson et al. (*PLoS Med*, 2017, 14(7):e1002310) and is described herein. The assay relies on detection of free $H_2S$ gas measured using a commercially available $H_2S$ detector (Z900XP, Environmental sensors, Boca Raton, Fla., USA). The default protocol is as follows:

- Dissolve compound (in room temperature phosphate-buffered saline (PBS), pH 7.4) to 10× stock solutions in Eppendorf tubes. The typical 10× stock concentration is 250 mM (1 M total sulfur).
- Vortex for 40 seconds.
- Invert the stock solution twice and then dilute 1/10 (0.5 into 4.5 ml) by rapidly transferring the stock into an airtight Falcon tube (50 ml) containing PBS that is typically pre-warmed to 37° C. using a water bath. The PBS into which the stock is diluted can be modified to be more or less acidic, or to contain thiols. The typical final concentration is 25 mM (100 mM total sulfur).
- Replace the Falcon tube cap, tighten and further seal the lid with parafilm. The liquid and gas (headspace) phases should constitute 5 and 45 ml, respectively.
- Typically incubate for an hour at 37° C.
- Remove from the water bath. Puncture one side of the Falcon tube lid with a 25-gauge needle.
- Puncture the other side of the Falcon tube lid with a 23-gauge needle attached to a 5 ml syringe. Push as far down into the headspace gas as possible, i.e. until the bevel of the needle. Slowly withdraw 5 ml headspace gas over 10 seconds.
- Pass the gas sample through the detector using a 3-way tap (closed to room air) to accommodate the syringe; this is attached to the detector inlet, as shown in FIG. 10. Once all of the gas has been drawn from the syringe, remove the syringe to allow room air to wash out the system. Failure to remove the syringe causes a build-up of $H_2S$ gas around the sensor leading to erroneously high readings.

Figure 11:
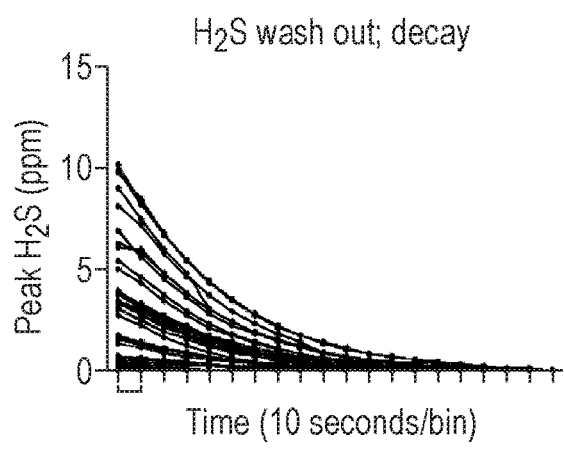
FIG. 11 shows a comparison of peak $H_2S$ values and the area under curve (AUC) during washout in the $H_2S$ gas detection assay. Values are recorded in parts per million (ppm).
Figure 11:
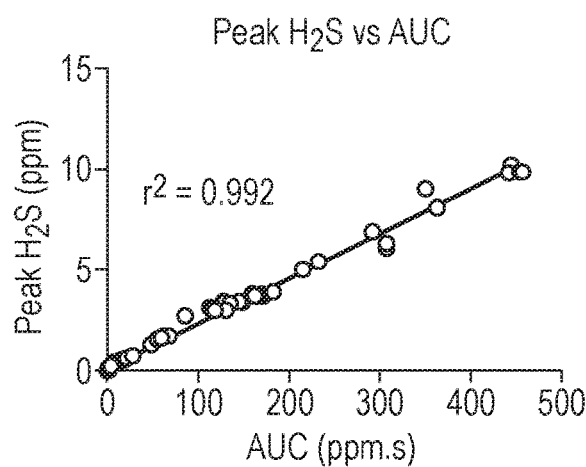

The Z900XP $H_2S$ detector displays a reading every 10 seconds. During the first series of experiments, both the peak $H_2S$ gas level (in parts per million, ppm) and every value during the wash out phase until the meter displayed zero were recorded. Typically, the peak $H_2S$ value is the first or second reading displayed after injection. If the sample is drawn in the latter part of the 10-second bin, the second or third reading may be the highest. A direct correlation (non-linear regression, straight line model, $r^2$=0.992; see FIG. 11) was observed on comparing the peak $H_2S$ value against the sum of the washout readings (decay) over time (area under curve, AUC). As the time to washout and the sum of values therein are directly proportional to the peak quantity of gas initially detected, it is appropriate to consider only the peak $H_2S$ gas level to determine the total amount of $H_2S$ gas release.

Figure 12A:
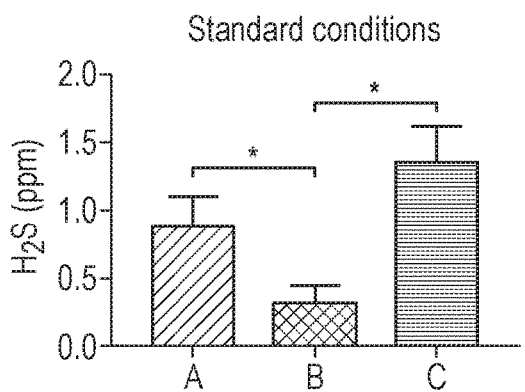
FIG. 12A shows the $H_2S$ gas release from salts A, B and C under standard conditions: dissolution in phosphate-buffered saline (PBS), incubation at 37° C. for 1 hour at pH 7.4.
Figure 12B:
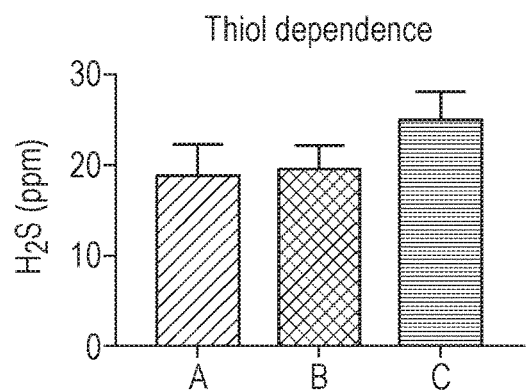
FIG. 12B shows the thiol dependence of $H_2S$ gas release from salts A, B and C following co-incubation with L-cysteine (5 mM).
Figure 12C:
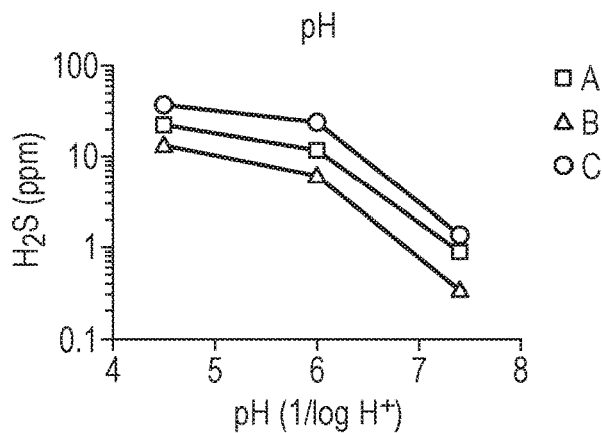
FIG. 12C shows the $H_2S$ gas release from salts A, B and C at pH 4.5, 6 and 7.4; pH was adjusted as required to 4.5 and 6 from the standard conditions by addition of aqueous HCl. n=3/group. * denotes P<0.05 using one-way ANOVA followed by Tukey's multiple comparisons test.

4.2 Release of $H_2S$ Gas from DEA-TTM Salts A, B and C Under Laboratory Conditions Initial testing of DEA-TTM salts A, B and C was carried out under standard conditions (dissolution in PBS, pH 7.4, incubation for 1 hour). The results are shown in FIG. 12A. The quantity of $H_2S$ released varied fourfold between the salts—salt C released the most $H_2S$ gas, whilst salt B released the least $H_2S$ gas. All three DEA-TTM salts exhibit striking thiol dependence, as shown in FIG. 12B. Co-incubation with L-cysteine (5 mM) elevates $H_2S$ gas release by 20-40 fold (for reference, the thiol dependence of ATTM showed a six-fold increase). The maximum $H_2S$ gas level observed from each of the three salts following incubation with thiols was comparable. All three DEA-TTM salts also exhibit pH dependence, as shown in FIG. 12C. Acidic conditions are shown to favour sulfide release. The level of $H_2S$ gas release increases with acidity, but the relative amounts of $H_2S$ gas released by each of salts A, B and C remain approximately similar at each pH to those levels observed under standard conditions (see FIGS. 12A and 12C).

4.3 Release of $H_2S$ Gas in Whole Blood Samples from Male Wistar Rats

Figure 13:
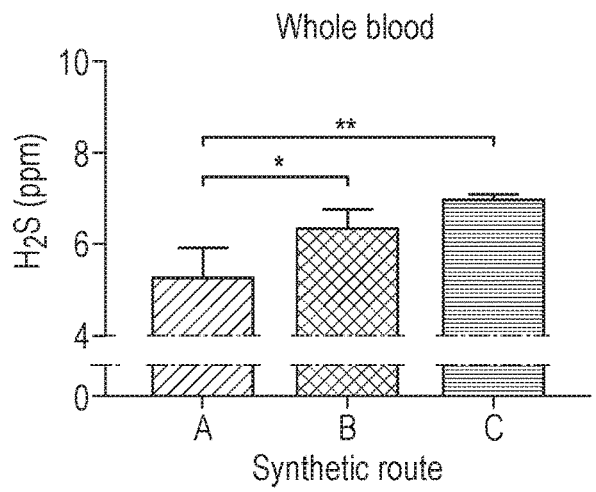
FIG. 13 shows the $H_2S$ release from DEA-TTM salts A, B and C in whole blood samples from male Wistar rats. n=3/group. * denotes P<0.05 and ** denotes P<0.01 using one-way ANOVA followed by Tukey's multiple comparisons test.

The release of $H_2S$ gas from DEA-TTM salts A, B and C in whole blood (anticoagulated with 2.5 mM ethylene-diamine-tetraacetic acid, EDTA) obtained from three anaesthetized male Wistar rats was also assessed. The assay was identical to that described above, with the exception that the 1/10 (0.5 into 4.5 ml) was diluted into airtight Falcon tubes (50 ml) containing pooled whole rat blood, rather than PBS. The blood into which the stock was diluted was pre-warmed to 37° C. using a water bath. $H_2S$ gas release from dissoluted DEA-TTM, diluted into rat blood, was measured as above. The least quantity of $H_2S$ gas was obtained from DEA-TTM synthesised by Route A (see FIG. 13). This was significantly lower than the quantity of $H_2S$ released by material from Routes B and C. A lower level of $H_2S$ gas release into the blood is highly desirable from a clinical perspective. Sulfide release or generation within the bloodstream is known to cause toxicity, principally related to hypotension. Most desirably, a sulfide donor administered to patients releases sulfide outside of the circulation, preferably intracellular, and more preferably inside the mitochondrion (at the site of intended action).

The invention claimed is:

1. A crystalline diethylamine tetrathiomolybdate salt, characterized by:
   (a) an XRPD pattern having at least three peaks selected from the peaks at 7.9, 11.4, 12.5, 13.9, 14.9, 20.8 and 21.5±0.5°2θ, wherein
      (i) the XRPD pattern has peaks at 11.4 and 14.9±0.2°2θ, wherein the peak at 11.4±0.2°2θ is at least one and a half times as intense as the peak at 14.9±0.2°2θ; or
      (ii) the XRPD pattern has peaks at 11.4 and 21.5±0.2°2θ, wherein the peak at 11.4±0.2°2θ is at least three times as intense as the peak at 21.5±0.2°2θ;
   (b) an XRPD pattern substantially similar to FIG. 1;
   (c) a $P2_1$ space group at a temperature of about 100 K;

(d) unit cell dimensions of a=7.1433(4) Å, b=10.7328(5) Å, c=10.7485(8) Å, α=90.00°, β=93.902(6)°, and γ=90.00° at a temperature of about 100 K; or (e) a combination thereof.

2. The crystalline diethylamine tetrathiomolybdate salt of claim 1, characterized by an XRPD pattern having at least three peaks selected from the peaks at 7.9, 11.4, 12.5, 13.9, 14.9, 20.8 and 21.5±0.2°2θ.

3. The crystalline diethylamine tetrathiomolybdate salt of claim 1, characterized either by:
   (i) an XRPD pattern having peaks at 11.4 and 14.9±0.2°2θ, wherein the peak at 11.4 ±0.2°2θ is at least one and a half times as intense as the peak at 14.9±0.2°2θ; or
   (ii) an XRPD pattern having peaks at 11.4 and 21.5±0.2°2θ, wherein the peak at 11.4 ±0.2°2θ is at least three times as intense as the peak at 21.5±0.2°2θ.

4. A pharmaceutical composition comprising a crystalline diethylamine tetrathiomolybdate salt as defined in claim 1, and a pharmaceutically acceptable diluent or carrier.

5. A method of treating a human or animal patient, wherein said method comprises administration of a therapeutically effective amount of a crystalline diethylamine tetrathiomolybdate salt according to claim 1, or a pharmaceutical composition according to claim 4, to a human or animal patient for treating a condition or disease requiring reduced metabolism of an organ or the whole body of a patient.

6. A process for making the crystalline diethylamine tetrathiomolybdate salt of claim 1, which comprises reacting ammonium tetrathiomolybdate with excess diethylamine, optionally wherein the ammonium tetrathiomolybdate is produced from the reaction of $(NH_4)_6Mo_7O_{24} \cdot 4H_2O$ with ammonium sulfide.

7. The method of claim 5, wherein the condition requiring reduced metabolism of an organ or the whole body of a patient is myocardial infarction (MI), stroke, severe haemorrhage or reperfusion injury.

8. The method of claim 5, wherein the condition to be treated is an acute condition.

9. The method of claim 5, wherein the crystalline diethylamine tetrathiomolybdate salt is administered to the patient dissolved in water or another physiologically acceptable aqueous media.

10. The method of claim 5, wherein the crystalline diethylamine tetrathiomolybdate salt or pharmaceutical composition is administered: (i) by bolus; (ii) by continuous infusion; or by a combination of (i) and (ii).

11. The method of claim 5, wherein the crystalline diethylamine tetrathiomolybdate salt or pharmaceutical composition is administered to the patient one or more times per day.

12. The method of claim 5, wherein the crystalline diethylamine tetrathiomolybdate salt or pharmaceutical composition is administered intravenously.

13. The method of claim 5, wherein a single administration of the crystalline diethylamine tetrathiomolybdate salt or pharmaceutical composition comprises from 0.1 to 10 mg DEA-TTM/kg body weight of the patient.

14. The method of claim 5, wherein a bolus comprising from 0.1 to 10 mg DEA-TTM/kg body weight of the patient is administered to the patient, and subsequently a continuous infusion comprising from 0.1 to 10 mg DEA-TTM/kg body weight of the patient is administered to the patient over a period of from 2 to 45 minutes.

\* \* \* \* \*